US006221643B1

(12) United States Patent
Ellis et al.

(10) Patent No.: US 6,221,643 B1
(45) Date of Patent: Apr. 24, 2001

(54) METHODS FOR DIAGNOSIS AND TREATMENT OF BLOOM'S SYNDROME

(75) Inventors: Nathan Ellis; James German, both of New York, NY (US); Joanna Groden, Cincinnati, OH (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 09/175,828

(22) Filed: Oct. 20, 1998

Related U.S. Application Data

(63) Continuation of application No. 08/559,303, filed on Nov. 15, 1995, now Pat. No. 5,824,501.

(51) Int. Cl.[7] ........................................................ C12N 9/14
(52) U.S. Cl. ............................................................. 435/195
(58) Field of Search ............................................... 435/195

(56) References Cited

PUBLICATIONS

Puranam et al. Cloning and characterization of RECQL, a potential human homologue of the *Escherichia coli* DNA helicase RecQ. J. Biol. Chem. (1994) 269(47):29838–45, Nov. 1994.*
Gangloff et al. The yeast type I topoisomerase Top3 interacts with Sgs1, a DNA helicase homolog: a potential eukaryotic reverse gyrase, Mol. Cell Biol. (Dec. 1994) 14(12):8391–8.*

Umezu et al. *Escherichia coli* RecQ protein is a DNA helicase. PNAS (Jul. 1990) 87(14):5363–7.*

* cited by examiner

*Primary Examiner*—Ponnathapu Achutamurthy
*Assistant Examiner*—Kathleen Kerr
(74) *Attorney, Agent, or Firm*—Amster, Rothstein & Ebenstein

(57) ABSTRACT

The present invention provides a method for diagnosing BS as well as determining whether a subject is a carrier of a mutated BLM gene. The present invention also provides one or more single-stranded nucleic acid probes and antibodies which may be formulated in kits, and used for diagnosing BS or determining whether a subject is a carrier of a mutated BLM gene. In addition, the present invention provides a method for treating or preventing the onset of BS in a subject in need of such treatment or prevention, as well as vectors and stem cells useful for such treatment or prevention. The present invention also provides a purified and isolated nucleic acid encoding an enzymatically active BLM protein, a vector comprising this nucleic acid, a cell stably transformed with this vector, as well as a method for producing recombinant, enzymatically active BLM protein. A purified, enzymatically active BLM protein is also provided by the present invention. Finally, the present invention provides a vector, an embryonic stem cell, and a non-human, transgenic animal, each of which comprises a mutated BLM gene, as well as a method for producing the non-human, transgenic animal.

9 Claims, 11 Drawing Sheets

```
    gcgcggcggccgtggttgcggcgcggaagtttggatcctgctggttccgtccgctaggagtctgctgctgcgaggattATGGCT    80
                                                                                    M  A
     GCTGTTCCTCAAAATAACTAGAGCAACTCAGCAACTTAATATAATTAAGTCTTCAAA                          160
  3  A  V  P  Q  N  N  L  Q  E  Q  L  E  R  H  S  A  R  T  L  N  N  K  L  S  L  S  K
     ACCAAATTTCAGTTTCACTTTTAAAAGAAAAACATCTTCAGATACAAGTATCTGTAACTGTGTCAGTGTCAGTAGCAA       240
 30  P  K  F  S  G  F  T  F  K  K  K  T  S  S  D  N  N  V  S  V  T  N  V  S  V  A
     AAACACCTGTATTAAGAAATAAAGATGTTAATGTTACGGAAGACTTTTCCTCAGTGAACCTCTACCACAACCACAAAT      320
 56  K  T  P  V  L  R  N  K  D  V  N  V  T  E  D  F  S  F  E  P  L  P  N  T  T  N
     CAGCAAAGGGTCAAGGACTTCTTTAAAATGCTCCAGGACAACAGAGAAACAGAGTGGATCAAAATCATTATTGCC         400
 83  Q  Q  R  V  K  D  F  F  K  N  A  P  A  G  Q  E  T  Q  R  G  G  S  K  S  L  L  P
     AGATTCTTCAGACTCCGAAGAAGTTGTATGCACTACCCAAAACACACCAACTGTAAAGAAATCCCGGGATACTGCTC      480
110  D  F  L  Q  T  P  K  E  V  V  C  T  T  Q  N  T  P  T  V  K  K  S  R  D  T  A
     TCAAGAAATTAGAATTCTTCACCAGATTCTTAAGTACCATCAATGATTGGGATGATATGGACTTTGATACT            560
135  L  K  K  L  E  F  S  S  P  D  S  L  S  T  I  N  D  W  D  D  M  D  F  D  T
     TCTGAGACTTCAAATCAATTGTACACCCCAAGTCACTTGTAAGAGTAAGCACTGCTCAGAAATCAA AAAGG           640
163  S  E  T  S  K  S  F  V  T  P  P  Q  S  H  F  V  R  V  S  T  A Q  K  S  K  K  G
     TAAGAGAAACTTTTTAAGCACTTTATACAGACTAAGACAGTGATTGCCTGATGAAGTTAAGCAGCGATGTCATGATGCCCC   720
190  K  R  N  F  F  K  A  Q  L  Y  T  T  N  T  V  K  T  D  L  P  P  S  S  E  S
     AGCAAATAGATTGACTGAGGAGCAGAAAGATGACTCAGGAAGTGCTCTGAAACTCATTGGAAGATGAAAGAGATAATAG     800
216  E  Q  I  D  L  T  E  E  Q  K  D  D  S  E  W  L  S  S  D  V  I  C  I  D  D  G  P
     ATTGCTGAAGTGCATATAAATGAAGATGCTCAGGAAAGTGACTCTCTGAAAACTCATCTTGAGGATGAAAGAGATAATAG     880
243  I  A  E  V  H  I  N  E  D  A  Q  E  S  D  S  L  K  T  H  L  E  D  E  R  D  N  S
     CGAAAA G AAGAATTTGAAGAATGAAGAAGCTGAAGAGCTTCATTCAACTGAGAAAGTTCCATGTATTGAATTGATGATGATT    960
270  E  K  K  N  L  E  E  A  E  L  H  S  T  E  K  V  P  C  I  E  F  D  D  D  D
     ATGATACGGATTTTGTTCCACCTTCTCCAGAAGAAATTATTTCTGCTTCTTCCTCCTCAAATGCTTAGTACGTTA           1040
296  Y  D  T  D  F  V  P  P  S  P  E  E  I  I  S  A  S  S  S  S  K  C  L  S  T  L
     AAGGACCTTGACACATCTGACAGAAGAGATGTTCTTAGCACATCTAGCACAAAGATCTTTTGTCAAAACTGAGAAAATGAG    1120
```

```
 696  S  L  C  Y  Q  L  P  A  C  V  S  P  G  V  T  V  V  I  S  P  L  R  S  L  I  V  D
      CAAGTCCAAAAGCTGACTCCTGGAGCATGTGTCTCCTGGAGATATATCCAGCTACATCTGATAAGACTCAGAAGCTACAAATAT  2320
 723  Q  V  Q  K  L  T  S  L  D  I  P  A  T  Y  L  T  G  D  K  T  D  S  E  A  T  N  I
      TTACCTCCAGTATCAAAAAGACCAATCATAAAACTTCTATATGTCACTGGAGACAAGACTGACTCAGAAGCTGCAAGTAACAGAC  2400
 750  Y  L  Q  L  S  K  K  D  P  I  I  K  L  L  Y  V  T  P  E  K  I  C  A  S  N  R
      TCATTCTACTCTGAGAATCTCTATGAGAGGAAGCTCTTGGCACGTTTGTTATTGATGAAGCACATTGTGTCAGTCAG  2480
 776  L  I  S  T  L  E  N  L  Y  E  R  K  L  L  A  R  F  V  I  D  E  A  H  C  V  S  Q
      TGGGGACATGATTTTCGTCAAGATTACAAAGAATGCTCCAGAAGTTCCTCTGTTCCGTGATGCTCT  2560
 803  W  G  H  D  F  R  Q  D  Y  K  R  M  N  M  L  R  Q  K  F  P  S  V  P  V  M  A  L
      TACGGCCACAGCTAATCCCAGGGTACAGAAGGACATCTGACTCAGTCAGCTGAAGATTCTCAGACCTCAGGTGTTAGCATGA  2640
 830  T  A  T  A  N  P  R  V  Q  K  D  I  L  T  Q  L  K  I  L  R  P  Q  V  F  S  M
      GCTTTAACAGACATATAATCTGAAATACTATGTCAGAAAAGCCTAAAAGGTGGCATTGATTGCCTAGAATGGATC  2720
 856  S  F  N  R  H  N  L  K  Y  Y  V  L  P  K  K  K  V  A  F  D  C  L  E  W  I
      AGAAAGCACCACCATATGATTCAGGGATAATTACTGCCTCCAGGCGAGAATGCTGACACGTTACA  2800
 883  R  K  H  H  P  Y  D  S  G  I  I  Y  C  L  S  R  R  E  C  D  T  M  A  D  T  L  Q
      GAGAGATGGCCTGCTGCTTGCTTACCATGCAGCTCTGGCCTCAGTGATTCTGCCAGATGAAGTGCAGCAGAAGTGGATTA  2880
 910  R  D  G  L  A  A  L  A  Y  H  A  G  L  S  D  S  A  R  D  E  V  Q  Q  K  W  I
      ATCAGGATGGCCTGTCAGTTATCTGTCATTGCTACAATTGCATTTGGAATGGGATTGACAAACCGGACGTGCGATTGTGATT  2960
 936  N  Q  D  G  C  Q  V  I  C  A  T  I  A  F  G  M  G  I  D  K  P  D  V  R  F  V  I
      CATGCATTCATCTCCCTAAATCTGTGGAGGTTACTACCAAGAATCTGGCAGAGCTGGAAGAGATGGGAAATATCTCACTG  3040
 963  H  A  S  L  P  K  S  V  E  G  Y  Y  Q  E  S  G  R  A  G  R  D  G  E  I  S  H  C
      CCTGCTTTCTATACCTATCATGATGTGACCAGACTGAAGAGACTTATAATGATGGAAAAGATGAAAACCATCATACAA  3120
 990  L  F  Y  T  Y  H  D  V  T  R  L  K  R  L  I  M  M  E  K  D  G  N  H  H  T
      GAGAAACTCACTTCAATAATTTGTATAGCATGGTACATTACTGTGAAATGTGAAATGCAGGAGAATACAGCTTTTG  3200
1016  R  E  T  H  F  N  N  L  Y  S  M  V  H  Y  C  E  N  I  T  E  C  R  R  I  Q  L  L
      GCCTACTTGGTGTGAAAATGGATTAATCCTGATTTTGTAAGAAACACCCAGATGTTTCTGTGATAATTGCTGTAAAAC  3280
1043  A  Y  F  G  E  N  G  F  N  P  D  F  C  K  K  H  P  D  V  S  C  D  N  C  C  K  T
```

```
                AAAGGATTATAAAACAAGAGATGTGACTGATGTGAAAAGTATTGTTCAAGAACATAGTTCATCACAAG 3360
1070            K  D  Y  K  T  R  D  V  T  D  D  V  K  S  I  V  R  F  V  Q  E  H  S  S  S  Q
                GAATGAGAAATATAAAACATGTAGTCCTTCTGGAAGATTTACTATGAATATGCTGGTCGACATTTCTGACATTTCTGGGGAGTAAG 3440
1096            G  M  R  N  I  K  H  V  G  P  S  G  R  F  T  M  N  L  V  D  I  F  L  G  S  K
                AGTGCAAAAATCCAGTCAGTCAGATTTGGATGAAGACTTATATATCAATGCCAGGCGATCGCTTATGTGATGCTGGAAATA 3520
1123            S  A  K  I  Q  S  G  I  F  G  K  G  S  A  Y  S  R  H  N  A  E  R  L  F  K  K  L
                GATACTTGACAAGATTTGGATGAAGACTTATATATCAATGCCAGGCGATCGCTTATGTGATGCTGGAAATA 3600
1150            I  L  D  K  I  L  D  E  D  L  Y  I  N  A  N  D  Q  A  I  A  Y  V  M  L  G  N
                AAGCCCAAACTGTACTAAATGCAATTTAAAGTAGACTTTATGCAAACAGAAATTCCAGCAGTGTCAAAAACAAAA 3680
1176            K  A  Q  T  V  L  N  G  N  L  K  V  D  F  M  E  T  E  N  S  S  V  K  K  Q  K
                GCGTTAGTAGCAAAGTGTCTCAGAGGAAGATGGTTAAAATGCCGTTAATACCGTCTACAGAAGTCTGCAAATCTCT 3760
1203            A  L  V  A  K  V  S  Q  R  E  E  M  V  K  K  C  L  G  E  L  T  E  V  C  K  S  L
                GGGGAAAGTTTGGTGTCATTACTTTGATGGTGTTACTGAAGACAAACTGAAAATATGGTGCGAAGTGATTCAGTATTA 3840
1230            G  K  V  F  G  V  H  Y  F  N  I  F  N  T  V  L  K  K  L  A  E  S  L  S  S
                ATCCTGAGGTTTGCTTCAAATTGATGGTGTTACTGAAGACAAACTGAAAATATGGTGCGAAGTGATTCAGTATTA 3920
1256            D  P  E  V  L  L  Q  I  D  G  V  T  E  D  K  L  E  K  Y  G  A  E  V  I  S  V  L
                CAGAAATACTCTGAATGACATCGCCAGTCCCCAGGATAAGTTCCCCAGGCAATAAGCCTGTCCAGCAGCAGAGCCCGGAAG 4000
1283            Q  K  Y  S  E  W  T  S  P  A  E  D  S  S  P  G  I  S  L  S  S  R  G  P  G  R
                AAGTGCCGCTGAGAGCTTGACGAGAGAAATACCGTATCTTCCACTACTTGCAAGTAAAACCAGAAATGAAAGGAAGA 4080
1310            S  A  E  E  L  D  E  E  I  P  V  S  S  H  Y  F  A  S  K  T  R  N  E  R  K
                GGAAAAAGATGCCAGCCTCCCAAGTCTAAGAGACAGAAAACTTCAAGGCAAGGGGTCTGCC 4160
1336            R  K  K  M  P  A  S  Q  R  S  K  R  K  T  A  S  S  G  S  K  A  K  G  G  S  A
                ACATGTAGAAGATATCTTCCAAAACGAAATCTTCCAGCATCATTGGATCCTCACATACTTCTCAAGCGAC 4240
1363            T  C  R  K  I  S  S  K  T  K  S  S  I  I  G  S  S  A  S  H  T  S  Q  A  T
                ATCAGGAGCCAATAGCAAATTGGGATTATGCCTCACCGAAGCCTATAAATGACCGTTTCTTAAGCCTTCATATGCAT 4320
1390            S  G  A  N  S  K  L  G  I  M  A  P  P  K  P  I  N  R  P  F  L  K  P  S  Y  A
                TCTCATAAcaaccgatctcaatgtacatagaccctctttgttgtcagcatctgtgactataagctg 4400
1416            F  S
                ttattcttgtatccaaaaaaaaaaaaaaaa 4437
```

FIG. 2D

```
                                             *                                     I
649  FPHTKEMMKIFHKKFGLHNFRTNQLEAINAALLGEDCFILMPTGGGKSLCYQLPACV-----SPGVTVVISPLRSLIVDQV  BLM
74   FPWSGKVKDILQNVFKLEKFRPLQLETINVTMAGKEVFLVMPTGGGKSLCYQLPALC-----SDGFTLVICPLISLMEDQL  REQL
659  YPWSDEVLYRLHEVFKLPGFRPNQLEAVNATLQGKDVFVLMPTGGGKSLCYQLPAVVKSGKTHGTTIVISPLISLMQDQV   SGS1
16   ---------VLQETFGYQQFRPGQEEIIDTVLSGRDCLVVMPTGGGKSLCYQIPALL-----LNGLTVVVSPLISLMKDQV  recQ II
725  QKLTSLDIPATYLTGDKTDSEATNIYLQLSKKDPIIKLLYVTPEKICASNRLISTLENLYERKLLARFVIDEAHCVSQWG  BLM
150  MVLKQLGISATMLNASSSKEHVKWVHDEMVNKNSELKLLYVTPEKIAKSKMFMSRLEKAYEARRFTRIAVDEVHCCSQWQ  REQL
739  EHLLNKNIKASMFSSRGTAEQRRQTFNLFIN--GLLDLVYISPEMISASEQCKRAISRLYADGKLARIVVDEAHCVSNWG  SGS1
83   DQLQANGVAAACLNSTQTREQQLEVMT--GCRTGQIRLLYIAPERL----MLDNFLEHL-AHWNPVLLAVDEAHCISQWG  recQ III           *
805  HDFRQDYKRMNMLRQKFPSVPVMALTATANPRVQKDILTQLKILRPQVFSMSFNRHNLKYYVLPKKPKKVA---FDCLEW  BLM
230  HDFRPDYKALGILKRQFPNASLIGLTATATNHVLTDAQKILCIEKCFFTTASFNRPNL--YYEVRQKPSNTEDFIEDIVKL REQL
817  HDFRPDYKELKFFKREYPDIPMIALTATASEQVRMDIIHNLELKEPVFLKQSFNRTNL--YYEVNKKTKNT---IFEICDA SGS1
157  HDFRPEYAALGQLRQRFPTLPFMALTATADDTTRQDIVRLLGLNDPLIQISSEDRPNIRY--MLMEKFKPLDQLM----RY recQ IV                                                  V
882  IRKHHPYDSGIIYCLSRRECDTMADTLQRDGLAALAYHAGLSDSARDEVQQKWINQDGCQVICATIAFGMGIDKPDVRFV  BLM
309  INGRYKGQSGIIYCFSQKDSEQVTVSLQNLGIHAGAYHANLEPEDKTTVHRKWSANE--IQVVATVAFGMGIDKPDVRFV  REQL
893  VKSRFKNQTGIIYCHSKKSCEQTSAQMQRNGIKCAYYHAGMEPDERLSVQKAWQADE--IQVICATVAFGMGIDKPDVRFV SGS1
233  VQEQ-RGKSGIIYCNSRAKVEDTAAALQSKGISAAAYHAGLENNVRADVQEKFQRDD-LQIVVATVAFGMGINKPNVRFV  recQ VI
962  IHASLPKSVEGYYQESGRAGRDGEISHCLLFYTYHDVTRLKRLIMMEKDGNHHTRETHFNNLYSMVHYCENITECRRIQL  BLM
388  IHHSMSKSMENYYQESGRAGRDDMKADCILYYGFGDIFRISSMVVMENVGQQ-------KLYEMVSYCQNISKSRRVLM   REQL
972  YHFTVPRTLEGYYQETGRAGRDGNYSYCITYFSFRDIRTMQTMIQKDKNLDRENKEKHLNKLQQVMAYCDNVTDCRRKLV  SGS1
311  VHFDIPRNIESYYQETGRAGRDGLPAEAMLFYDPADMAWLRRCLEEKPQGQLQDIERH--KLNAMGAFAEAQT-CRRLVL  recQ
```

FIG. 4

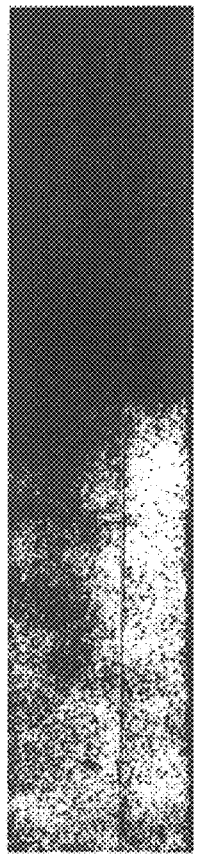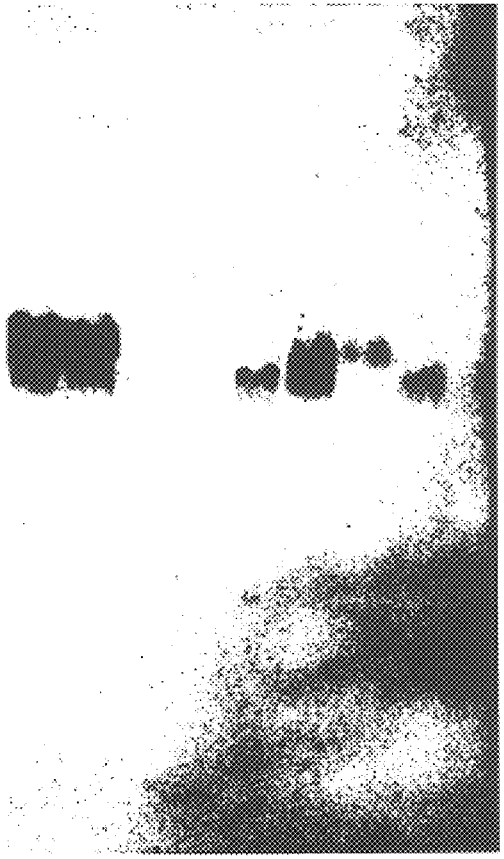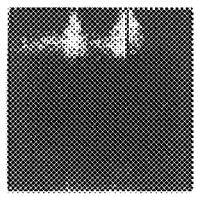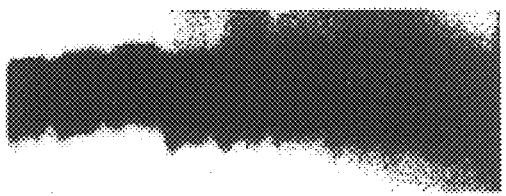
FIG. 5A  FIG. 5B

METHODS FOR DIAGNOSIS AND TREATMENT OF BLOOM'S SYNDROME

CROSS-REFERENCE TO RELATED APPLICATIONS

This is a continuation of U.S. application Ser. No. 08/559,303, filed Nov. 15, 1995, now U.S. Pat. No. 5,824,501, the contents of which is hereby incorporated by reference in its entirety.

STATEMENT OF GOVERNMENT INTEREST

This invention was made with government support under NIH Grant Nos. HD 04134, CA 50897 and GM 47890. As such, the government has certain rights in this invention.

BACKGROUND OF THE INVENTION

This invention is based upon the discovery by the inventors of the gene associated with Bloom's syndrome ("BS"), the "BLM gene" or "BLM", and a novel protein encoded by this gene. The discovery of the BLM gene and the protein encoded by the gene will have important implications in the diagnosis and treatment of BS, the recognition of carriers of mutations at BLM, and more broadly in the development of new cancer diagnostics and therapeutics.

BS is a rare autosomal recessive trait characterized clinically by growth deficiency, a sun-sensitive telangiectatic erythema of the face, immunodeficiency, and male infertility (German, J. *Medicine* 72:393–406 (1993)). Somatic cells from persons with BS are characterized by a striking genomic instability, and display an increased frequency of chromosome abnormalities (breaks, gaps and rearrangements) and inter- and intramolecular exchanges, including sister-chromatid exchanges (Ray, J. H. and German, J. (1983) The cytogenetics of the "chromosome-breakage syndromes." In: German J. (ed.) Chromosome mutations and neoplasia. Alan R. Liss, New York, pp. 135–168). The hypermutability of BS cells is responsible for the benign and malignant neoplasms in BS patients that arise at unusually early ages and in excessive numbers (German, 1993, supra).

Complementation analyses have established that a single locus, designated BLM, is mutated in BS (Weksberg, R., et al. *Am. J. Hum. Genet.* 42:816–824 (1988)). The BLM locus has been assigned to human chromosome 15 (McDaniel, L. D., and Schultz, R. A. *Proc. Natl. Acad. Sci. USA* 89:7968–7972 (1992)), and regionally mapped to chromosome band 15q26.1 based upon tight linkage to FES by homozygosity mapping (German, J., et al. *Proc. Acad. Natl. Sci. USA* 91:6669–6673 (1994)). Prior to the present invention, however, the BLM gene had not been identified.

SUMMARY OF THE INVENTION

The present invention provides a method for diagnosing BS in a subject comprising detecting the presence of two mutated BLM genes or the absence of a wild type BLM gene in nucleic acid of the subject. The present invention also provides a method for determining whether a subject is a carrier of a mutated BLM gene comprising detecting the presence of a mutated BLM gene in nucleic acid of the subject.

The present invention further provides one or more single-stranded nucleic acid probes which specifically hybridize to the wild type BLM gene or the mutated BLM gene, and mixtures thereof, which may be formulated in kits, and used for diagnosing BS or determining whether a subject is a carrier of the mutated BLM gene.

In addition, the present invention provides an antibody immunoreactive with a wild type BLM protein, as well as an antibody immunoreactive with a mutant BLM protein, which may be formulated in kits, and used for diagnosing BS or determining whether a subject is a carrier of the mutated BLM gene.

The present invention also provides a method for treating or preventing the onset of BS in a subject in need of such treatment or prevention comprising the delivery and expression of a functional BLM gene into a sufficient number of cells of the subject to treat or prevent the onset of BS in the subject. A stem cell which expresses the BLM gene introduced therein through viral transduction, homologous recombination or transfection is also provided by the invention.

The present invention further provides a recombinant viral vector for treating a defect in the BLM gene in a target cell comprising (a) the nucleic acid of or corresponding to at least a portion of the genome of a virus, which portion is capable of directing the infection of the target cell, and (b) a BLM gene operably linked to the viral nucleic acid and capable of being expressed as a functional gene product in the target cell.

The present invention still further provides a purified and isolated nucleic acid encoding an enzymatically active BLM protein, a vector comprising this nucleic acid, a cell stably transformed with this vector, as well as a method for producing recombinant, enzymatically active BLM protein. A purified, enzymatically active BLM protein is also provided by the present invention.

Finally, the present invention provides a vector and an embryonic stem cell each of which comprises a mutated BLM gene, a non-human, transgenic animal whose germ and somatic cells contain a mutated BLM gene sequence introduced into said animal, or an ancestor thereof, at an embryonic stage, as well as a method for producing the non-human, transgenic animal.

Additional objects of the invention will be apparent from the description which follows.

BRIEF DESCRIPTION OF THE FIGURES

FIG. 2 is depictive of the 4,437-bp H1–5' sequence, which represents the merged sequences of the H1 cDNA and the 5' clones, with its encoded 1,417-residue amino acid sequence (single-letter code). Nucleotides in the open reading frame starting at the first in-frame ATG, 75 bp from the first nucleotide of the H1–5' sequence, are capitalized. The in-frame nonsense codon (TAA) marked by a period is followed by 88 nucleotides of 3' untranslated sequence. At the initiator methionine, there is a Kozak consensus sequence (Kozak, M. J. Cell Biol. 108:229–241 (1989)), and an acceptable polyadenylation sequence (underlined) is present 20-bp upstream of a 21-bp polyA tail. Sites at which substitution or deletion were detected in persons with BS (see Table 1) are boxed, and a site at which an insertion was identified is marked by a diamond. The EagI and SmaI sites used in the construction of a full-length cDNA referred to as B3 (see Experimental Details Section) are overlined. Asterisks mark amino acid identities to three motifs present in the RNA polymerase II largest subunit.

FIG. 4 represents the amino acid sequence homologies in the seven conserved helicase domains between the putative peptide encoded by the H1–5' sequence and by the three other known members of the RecQ subfamily of helicases. The numbers (left) indicate amino acid positions in each peptide, and gene product names are at the right. Sequence alignments were performed by the Megalign computer program (DNAStar); dashes indicate gaps inserted by the program to maintain alignment. Amino acid residues that are identical at a position between sequences are shaded. Two different shadings are used when at a position two pairs of identical amino acids were observed. Overlined sequences mark the seven helicase domains (Gorbalenya, A. E., et al. Nucl. Acids Res. 17:4713–4730 (1989)). The DEXH box is in helicase domain II. Asterisks denote positions at which putative missense mutations were identified. The candidate gene product is referred to here as BLM because mutations have been discovered in the gene in persons with BS (see text).

FIGS. 5A and 5B represent the Northern analysis of the H1–5' sequences expressed in cultured cells. In FIG. 5A, RNA preparations were analyzed from HG2162, a normal LCL; HG2635, a normal diploid fibroblast cell line; and HeLa cells. In FIG. 5B, RNA preparations were analyzed from HG 1943 and HG2162—normal LCLs—and HG2703, HG1584, HG1987, HG1972, HG2231, HG1626, HG2820— BS LCLs. Thirty micrograms of total RNA from each cell line was loaded in each lane. Labeled probes—the H1 cDNA (upper panels) and a cDNA for G3PDH (lower panels)— were hybridized to membranes of the blotted gels and, after washing, the membranes were exposed from one to three days (FIG. 5A) or for 15 minutes (FIG. 5B). On a 7-day exposure, faint bands resembling the hybridization pattern in normal cells were detected at the 4.5-kb position in HG2703, HG1584, and HG2820. The LCLs developed from persons with BS are shown in Table 1, except HG2703, [NR2 (CrSpe)]; and HG2820, [142(MaMatu)].

DETAILED DESCRIPTION OF THE INVENTION

Figure 1A:
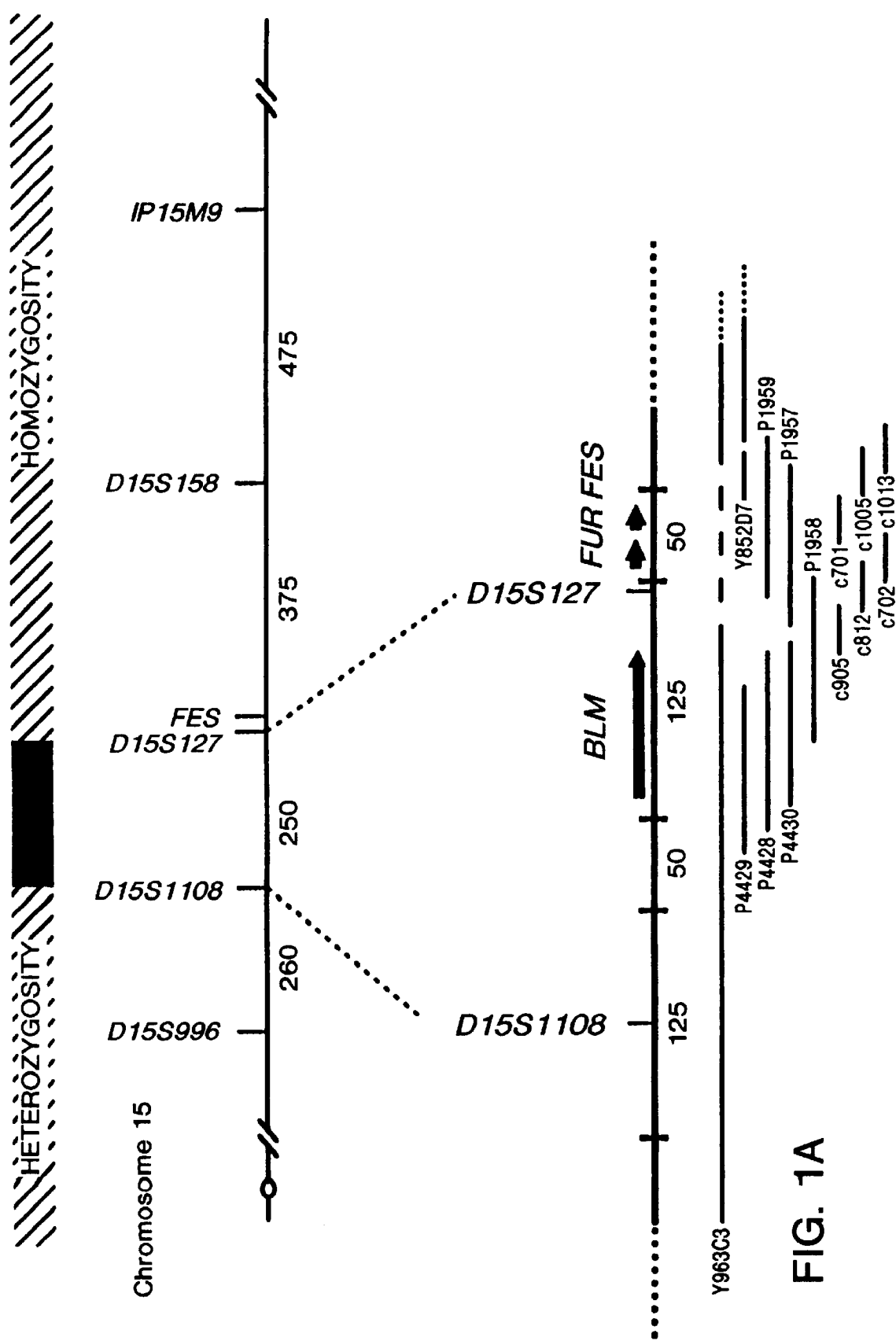
FIG. 1A represents the genetic map of the BLM region of 15q. On the upper horizontal line, the order and distances (shown in kilobase "kb") between the polymorphic microsatellite loci were estimated by long-range-restriction mapping (Straughen, J., et al. Physical mapping of the region containing the Bloom's syndrome gene BLM by the identification of YAC and P1 clones from human chromosome 15. Genomics, 1995, submitted). The distance between D15S127 and FES (not indicated) was determined to be 30 kb by restriction enzyme mapping of a cosmid contig (see below). Vertical lines indicate the position of the marker loci, and the circle represents the centromere. The interval between loci D15S1108 and D15S127 is expanded below the map. Vertical lines intersecting mark the unmethylated CpG-rich regions identified by long-range restriction mapping, and arrows indicate the direction of transcription of three genes in the region. Certain YACS, Pls, and cosmids (Y, P, and c, respectively) from the contig (Straughen, et al., supra) are depicted by horizontal lines underneath the map. Dashes on the YAC lines indicate internal deletions. At the top of the figure, the horizontal cross-hatched bars indicate regions proximal to BLM that remained heterozygous in the low-SCE LCLs and regions distal to BLM that had become homozygous. The minimal region to which BLM was thus assigned by SCP mapping is represented in black.

The present invention provides a method for diagnosing BS in a subject comprising detecting the presence of two mutated BLM genes or the absence of a wild type BLM gene in nucleic acid of the subject. The present invention also provides a method for determining whether a subject is a carrier of a mutated BLM gene comprising detecting the presence of a mutated BLM gene in nucleic acid of the subject.

As used herein, the "mutated BLM gene" is the mutated form of the normal BLM gene, which contains one or more deletion, insertion, point or rearrangement mutations, or a combination thereof, that may result in loss or alteration of activity of the gene product expressed by the mutated BLM gene. A subject who inherits a copy of the mutated BLM gene on each chromosome 15 has clinical BS. The "wild type BLM gene" is the normal form of the gene which expresses an enzymatically active gene product. The wild type BLM gene is present in subjects who are not carriers of the mutated BLM gene, and is the preferentially expressed gene in subjects who are carriers of the mutated BLM gene.

The methods of the present invention may be used to determine whether persons in the population at large are carriers of the mutated BLM gene or have BS, for identifying persons at risk in developing the disease, i.e. relatives of persons with BS, as well as for confirming diagnosis of BS. The methods of the present invention are also useful for identifying couples who are carriers of the mutated BLM gene and thus at risk for propagating offspring who will have BS, as well as for identifying embryos or fetuses which may be born with BS. Accordingly, as used herein, "subject" may be an embryo, fetus, newborn, infant or adult.

The presence of the mutated BLM gene(s) (or the absence of the wild type BLM gene) may be detected by procedures known in the art including but not limited to standard sequencing techniques (e.g. dideoxy chain termination), restriction enzyme digestion analysis, hybridization with one or more probes hybridizable to the mutated and/or wild type BLM gene using standard procedures such as Southern blot analysis, polymerase chain reaction using sense and antisense primers prepared from the mutated and/or wild type BLM genes, and combinations thereof.

The presence of the mutated BLM gene(s) (or the absence of the wild type BLM gene) also may be detected by detecting expression of the gene product of the gene. Such expression products include both MRNA as well as the protein product itself. mRNA expression may be detected by standard sequencing techniques, hybridization with one or more probes hybridizable to the mutated and/or wild type BLM MRNA using standard procedures such as Northern blot analysis, dot and slot hybridization, S1 nuclease assay, or ribonuclease protection assays, polymerase chain reaction using sense and antisense primers prepared from the mutated and/or wild type BLM genes, and combinations thereof. The protein may be detected using antibodies to the protein expressed by the mutated BLM gene and/or the wild type BLM gene by procedures known in the art including but not limited to immunoblotting, immunoprecipitation, solid phase radioimmunoassay (e.g. competition RIAS, immobilized antigen or antibody RIAs, or double antibody RIAs), enzyme-linked immunoabsorbent assay, and the like.

The present invention also provides single-stranded nucleic acid probes and mixtures thereof for use in diagnosing BS and/or determining whether an individual is a carrier of the mutated BLM gene. The nucleic acid probes may be DNA, cDNA, or RNA, and may be prepared from the mutated and/or wild type BLM gene. The probes may be the full length sequence of BLM gene, or fragments thereof. Typical probes are 12 to 40 nucleotides in length. Generally, the probes are complementary to the BLM gene coding sequences, although probes to introns are also contemplated. The probes may be synthesized using an oligonucleotide synthesizer such as Applied Biosystems Model 392 DNA/RNA synthesizer, and may be labeled with a detectable marker such as a fluorescence, enzyme or radiolabeled markers including $^{32}$p and biotin, and the like. Combinations of two or more labelled probes corresponding to different regions of the BLM gene also may be included in kits to allow for the detection and/or analysis of the BLM gene by hybridization.

The present invention also provides antibodies immunoreactive with the protein expressed by the wild type BLM gene (and analogues thereof), as well as antibodies immunoreactive with the protein expressed by the mutated BLM gene. The antibodies may be polyclonal or monoclonal and are produced by standard techniques. The antibodies may be labeled with standard detectable markers (e.g. chemiluminescent detection systems and radioactive labels such as $^{125}$I) for detecting the wild type and mutated BLM genes. The antibodies also may be presented in kits with detectable labels and other reagents and buffers for such detection.

The present invention also provides a method for treating or preventing the onset of BS in a subject in need of such treatment or prevention comprising the delivery and expression of a functional BLM gene into a sufficient number of cells of the subject, preferably bone marrow stem cells, to treat or prevent the onset of BS in the subject. As used herein, "functional BLM gene" is a gene which when incorporated into a cell's nucleic acid expresses a functional gene product, and includes the wild type BLM gene as well as variations thereof. The delivery and expression of the functional BLM gene may be accomplished by introducing the functional BLM gene into the cells or by correcting the mutation(s) in the subject's BLM gene.

The functional BLM gene may be delivered into the subject's cells by a number of procedures known to one skilled in the art, e.g. electroporation, DEAE dextran, cationic liposome fusion (using both monocationic and polycationic lipids), protoplast fusion, DNA coated microprojectile bombardment, injection with recombinant replication-defectiveretroviruses, homologous recombination, and the like. Accordingly, a stem cell which expresses the BLM gene introduced therein through viral transduction, homologous recombination, or transfection is also provided by the present invention.

The present invention also provides a recombinant viral vector for treating a defect in the BLM gene in a target cell comprising (a) the nucleic acid of or corresponding to at least a portion of the genome of a virus, which portion is capable of directing the infection of the target cell, and (b) a functional BLM gene operably linked to the viral nucleic acid and capable of being expressed as a functional gene product in the target cell. The recombinant viral vectors of the present invention may be derived from a variety of viral nucleic acids known to one skilled in the art, e.g. the genomes of HSV, adenovirus, adeno-associated virus, Semiliki Forest virus, vaccinia virus, and other retroviruses or DNA viruses.

In addition, the present invention provides a purified and isolated nucleic acid encoding an enzymatically active BLM protein, which may be the wild type protein or an analogue thereof, and includes all nucleic acid sequences encoding such enzymatically active proteins, including substitutions due to the degeneracy of the genetic code. The nucleic acid may be genomic DNA, cDNA or RNA. In the preferred embodiment, the nucleic acid encodes the amino acid sequence contained in FIG. 2. In the particularly preferred embodiment, the nucleic acid has the nucleotide sequence contained in FIG. 2.

The present invention also provides a vector comprising nucleic acid encoding an enzymatically active BLM protein, as well as a cell stably transformed with the vector. The vector may be any plasmid, viral-derived nucleic acid, lytic bacteriophage derived from phage lambda, cosmid, filamentous single-stranded bacteriophage such as M13, and the like, for cloning nucleic acid or introducing the nucleic acid into a cell for expression. The cell may be eukaryotic or prokaryotic. Suitable host cells include but are not limited to bacterial cells such as *E. coli, Bacillus subtilis, Agrobacte-*

*rium tumefaciens, Bacillus subtilis, Agrobacterium tumefaciens, Bacillus megaterium,* eukaryotic cells such as *Pichia pastoris, Chlamydomonas reinhardtii, Cryptococcus neoformans, Neurospora crassa, Podospora anserina, Saccharomyces cerevisiae, Saccharomyces Dombe, Uncinula necator,* cultured insect cells, cultured chicken fibroblasts, cultured hamster cells, cultured human cells such as HT1080, MCF7, 143B and cultured mouse cells such as EL4 and NIH3T3 cells. Such expression systems may be used to produce a recombinant, enzymatically active BLM protein by culturing a cell transformed with a vector comprising a nucleic acid encoding an enzymatically active BLM protein, and recovering BLM protein from the culture.

The present invention also provides a purified enzymatically active BLM protein. The protein may be the wild type protein or an analogue thereof. As used herein, "analogue" means functional variants of the wild type protein, and includes BLM proteins isolated from mammalian sources other than human, as well as functional variants thereof. The protein also may be isolated from native cells or recombinantly produced. Preferably, the protein has the amino acid sequence contained in FIG. 2.

The present invention also provides a vector for use in preparing a non-human, transgenic animal comprising a mutated BLM gene which is capable of introducing the mutated BLM gene in at least some embryonic cells to which the vector is introduced, an embryonic stem cell comprising a mutated BLM gene which has been integrated into the cell following transduction with the vector above, as well as a non-human transgenic animal of BS which would be useful for studying BS as well as cancer in general. The mutated BLM gene may be integrated into the germ line of a non-human animal such as a mouse, rat, goat, sheep or other non-human species in order to obtain a transgenic animal model by methods known in the art (see Alberts, B., et al. *Molecular Biology of the Cell,* 2d. Garland Publ. Inc., New York and London, pp. 267–269 (1989)). For example, nucleic acid encoding the mutated BLM protein can be inserted into the genome of a replication-defective virus such as HSV or a retrovirus or transposen and the resultant construct injected into embryonic stem cells. Alternatively, the transgenic animal may be made by injecting nucleic acid into the male pronucleus of a fertilized egg of a nonhuman animal, transplanting the "transgenic embryo" into a pseudopregnant female and then analyzing offspring for the presence of the injected nucleic acid in their genome.

Based upon the high incidence of a variety of tumors in a variety of tissues in a BS patient which appears to model cancer development in the general population (German, J. *Medicine* 72:393–406 (1993)), the identification of the BLM gene and its gene product should be useful for developing diagnostics and therapeutics for cancer in the population at large.

The present invention is described in the following Experimental Details Section, which is set forth to aid in an understanding of the invention, and should not be construed to limit in any way the invention as defined in the claims which follow thereafter.

Experimental Details Section

I. Materials and Methods

A. Subjects and Samples

The persons with BS in whom low-SCE lymphocytes have arisen were described previously (German, J., et al. Bloom's syndrome. XIX. Cytogenetic and population evidence for genetic heterogeneity. *Clin. Genet.,* 1995, in press). Epstein-Barr virus transformed lymphoblastoid cell lines (LCLs) were developed from these and other persons with BS by standard culture methods using material obtained through the Bloom's Syndrome Registry (German and Passarge, supra). The recombinant low-SCE LCLs in which reduction to homozygosity had been detected, and the cells used to determine the constitutional genotypes of the five persons from whom these recombinant low-SCE LCLs were developed, also have been described (Ellis, et al. *Am. J. Hum. Genet.,* 1995, supra). The polymorphic loci typed included some previously reported (Beckmann, J. S., et al. *Hum. Mol. Genet.* 2:2019–2030 (1993); Gyappay, G., et al. *Nature Genetics* 7:246–339 (1994)) and others that were identified during the physical mapping of the BLM region of chromosome 15 (Straughen, et al., supra). The methods of preparation of DNA samples, oligonucleotide primers, and conditions for PCR amplification of microsatellite polymorphisms on chromosome 15 have been described (German, et al., 1994, supra; Ellis, N. A., et al. *Am. J. Hum. Genet.* 55:453–460 (1994); Straughen, et al., supra).

B. Direct cDNA Selection

Direct cDNA selection was carried out as described by Parimoo, S., et al. (*Proc. Natl. Acad. Sci. USA* 88:9623–9627 (1991)). Briefly, DNAs (15 ng) from commercial lambda cDNA libraries prepared from cultured foreskin fibroblasts (Clontech) and Jurkat cells (Stratagene) were amplified by PCR (94° C. 1 min, 55° C. 1 min, 72° C. 2 min and 10 sec for 32 cycles) using primer set A (GGTGGCGACGACTCCTGGA and ACCAGACCAACTGGTAATG) for the fibroblast cDNA library and the universal forward and reverse M13 sequencing primers for the Jurkat cDNA library under standard conditions with Taq polymerase (Boehringer Mannheim). EcoRI-digested cosmid (c905) or P1 (P1958) DNAs (100 ng) bound to Hybond N membrane in 10×SSC, were denatured in 0.5 M NaOH/1.5 M NaCl, neutralized in 0.5 M Tris-HC1 pH 7.2/1.5 M NaCl, and fixed by UV-crosslinking. Hybridization of the PCR-amplified cDNAs to repetitive sequences on the cosmid and P1 clones was blocked by prehybridizing the membranes with Cot1 DNA (25 ng/m; Gibco, BRL), poly(dI):poly(dC) (20 ng/µl; Pharmacia), vector DNA (pWE15 or pAD10SacBII at 25 ng/µl in 5×SSPE, 5×Denhardt's solution, and 0.5% SDS at 65° C. overnight. Hybridization of the PCR-amplified cDNAs (25 ng/µl) was at 65° C. for 2 days in the same solution without poly(dI):poly(dC). The membranes were washed, and without elution the bound cDNAs were amplified by PCR with primer set A, followed by nested PCR with primer set B (ATGGTAGCGACCGGCGCTCA and CCGTCAGTATCGGCGGAATT) for the fibroblast library and the T3 and T7 sequencing primers for the Jurkat library. A sample of the PCR product after each amplification was analyzed by agarose gel electrophoresis, and another was cloned into Bluescript. Independent clones were picked at random, plasmid DNAs prepared, and insert sizes were determined by restriction enzyme digestion and agarose gel electrophoresis. Inserts from selected clones were purified and used as hybridization probes against all of the other clones as well as against selected genomic DNAs to determine the chromosomal origin of the sequences (see below). The enrichment procedure was repeated and the selected cDNA clones analyzed again. The fibroblast cDNA clone 905-28 was obtained after two rounds of selection (250,000-fold enriched), and was sequenced by the dideoxy chain-termination technique (Sanger, F., et al. *Proc. Natl. Acad. Sci.* 74:55463–5467 (1977); Tabor, S., and Richardson, C. C. *Proc. Natl. Acad. Sci. USA* 84:4767–4771 (1987)).

The genomic origin of clones isolated by direct selection were verified by hybridization of inserts to Southern blots of DNAs from the following: clones in the contig; human cells; and two human x hamster somatic cell hybrids, one of which contains an intact chromosome 15 as the only human chromosome present (GS89K-1; Warburton, D., et al. *Genomics* 6:358–366 (1990)) and one in which the only chromosome 15 material present had, through a translocation, lost all the sequences distal to band 15q25 (GM10664, obtained from NIGMS Human Genetic Mutant Cell Repository at the Cornell Institute of Medical Research).

C. cDNA Cloning, 5'-RACE, and cDNA Secuencing

The selected cDNA 905-28 was hybridized to $10^6$ clones from a HeLa cDNA library (Stratagene) according to standard procedures (Sambrook, J., Fritsch, E. F., and Maniatis, T. (1989) Molecular Cloning. A Laboratory Manual. 2nd edition, Cold Spring Harbor University Press). Twenty-eight lambda clones were isolated and converted to Bluescript plasmids by superinfection with ExAssist helper phage (Stratagene). DNA was prepared and 15 independent size-classes of clones were identified. The 5'-end of a clone from each class was sequenced with Bluescript SK sequencing primer. To extend the sequence, two oligonucleotides were synthesized from the beginning and the end of each of the 5' sequences, and sequencing was performed on the largest cDNA clone obtained by hybridization (clone H1). This procedure provided sequences from both DNA strands for most of the H1 cDNA. Ambiguous segments were determined by sequencing with specific oligonucleotides.

Figure 2B:
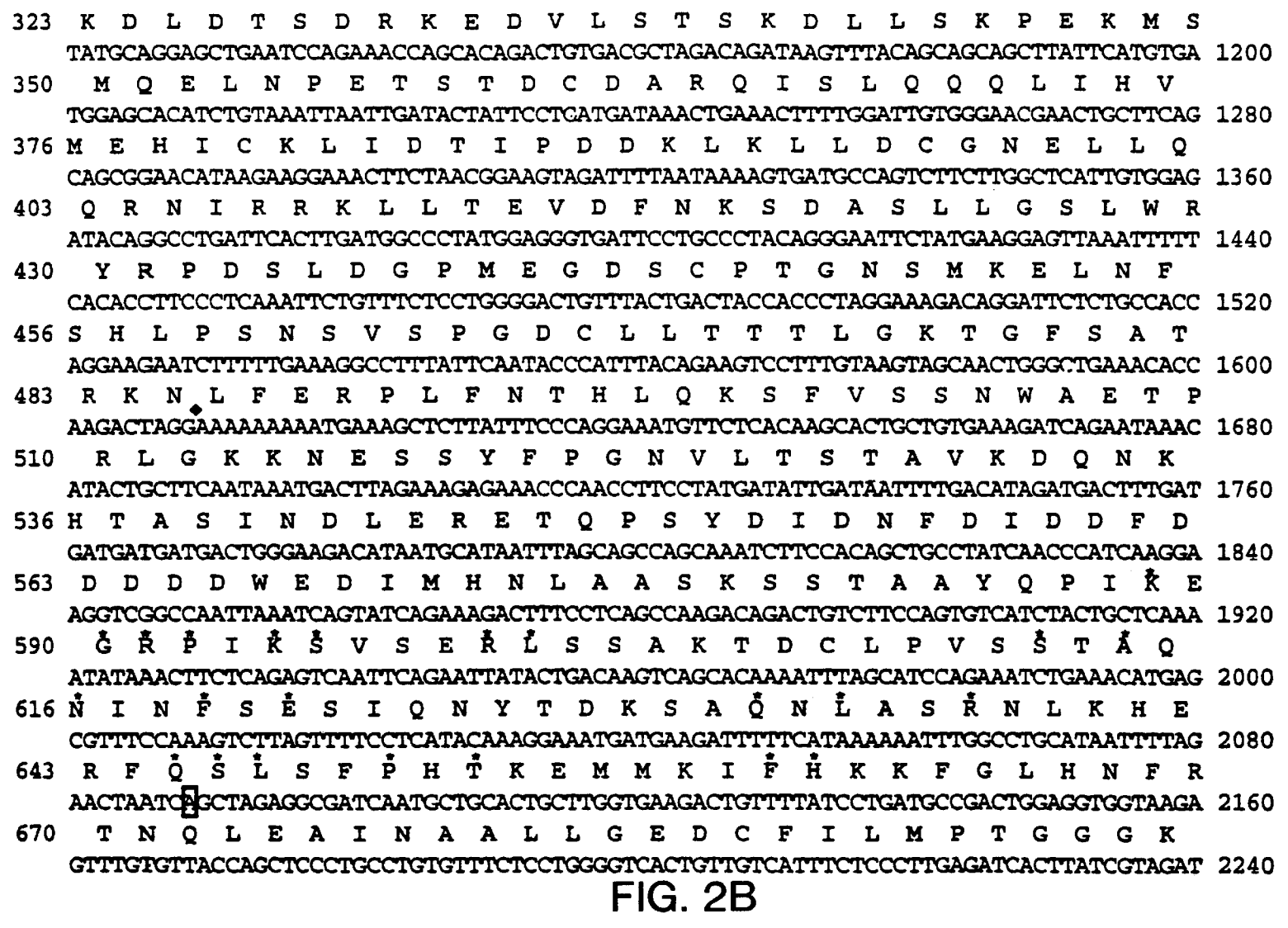

Because the reading frame was open at the 5' end of the H1 clone, additional upstream sequences were obtained by a PCR method. PCR was carried out on DNA prepared from the HeLa cDNA library using an oligonucleotide (Y177, TTGTGGTGTTGGGTAGAGGTT) 8 bp from the 5' end of H1 and the T3 sequencing primer. The PCR products were cloned into pT7Blue (Novagen), 18 clones were isolated, and the 8 largest inserts were sequenced. The three largest of these clones (5'–5, 5'–15, and 5'–17) extended the sequences 289 bp 5' of the H1 cDNA. The complete cDNA sequences present in the HeLa library are referred herein as H1–5' (FIG. 2). Database searches then were carried out according to the method of Altschul, S. F., et al. (*J. Mol. Biol.* 215:403–410 (1990)) using segments of the predicted amino acid sequence encoded in the HI-5' sequence as queries against the collected amino acid sequence databases that are accessible through the National Library of Medicine.

A full-length clone referred to as B3 was constructed by performing PCR of HeLa library DNA using an oligonucleotide (Y180, GCCGCCGGCACCAAC) from the 5' end of the H1–5' sequence and an internal oligonucleotide (BC13, CCTCAGTCAAATCTATITGCTC) which permitted amplification of a 739-bp product. EagI and SmaI sites (FIG. 2) were used to clone the product into NotI/SmaI-digested H1 DNA.

Figure 3:
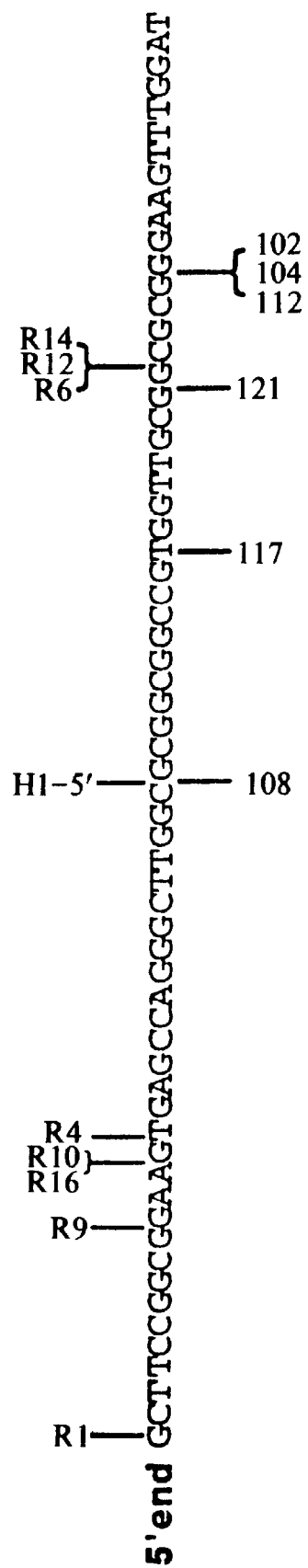
FIG. 3 is depictive of the nucleotide sequence of the 5' end of the candidate gene determined by cDNA analysis and 5'-RACE experiments. The sequence of the longest cDNA isolated (clone R1) is shown. The sequences were obtained by analysis of 11 lymphoblastoid cDNAs (clone names prefixed by an R), identified by screening 8×10$^6$ clones with a EagI/SmaI DNA fragment from the 5' part of the H1–5' sequences (FIG. 2), and of 12 5'-RACE clones amplified from fibroblast cDNA with nested PCR primers (Experimental Details Section). Vertical lines mark the nucleotides at which nine lymphoblastoid cDNA (clones named above the sequences) and six cloned 5'-RACE fragments (clones named below the sequences) initiated. Three cDNA and six 5'-RACE clones not shown contained sequences which initiated less than 38 bp upstream of the first in-frame ATG. The sequences at the 5' end are G+C-rich (71%), perhaps explaining the absence of in-frame nonsense codons upstream of the first in-frame ATG.
Figure 6A:
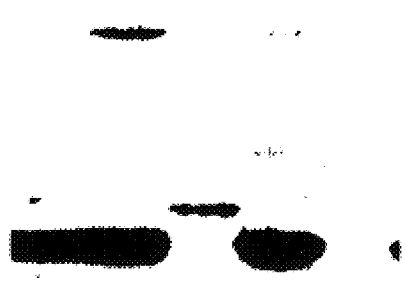
FIGS. 6A–6E represent the novel SSCP conformers detected in cDNA samples isolated from BS LCLs after PCR-amplification of the BLM gene. Each figure includes five lanes of cDNAs from five unrelated persons with BS amplified with oligonucleotides designed from a unique region of the BLM gene. The novel conformers in which mutations were detected are shown in the center lanes of each FIG.: 6A, BS LCL HG1514 from 15(MaRo); 6B, BS LCL HG1624 from 113(DaDem); 6C, BS LCL HG1926 from 97(AsOk); 6D, BS LCL HG2231 from 139 (ViKre); 6E, BS LCL HG1626 from 93 (YoYa). Not shown are novel conformers in 92(VaBi) and 112(NaSch).
Figure 6B:
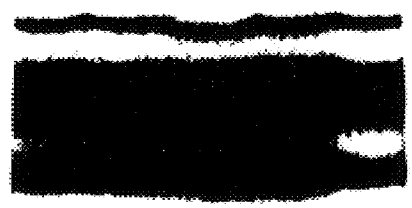
Figure 6C:
Figure 6D:
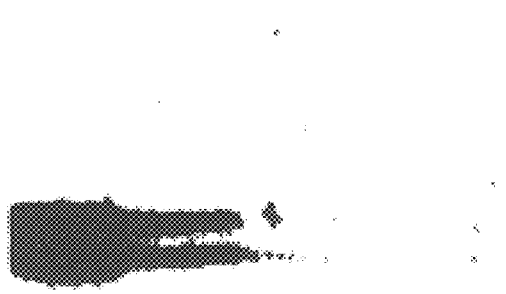
Figure 6E:
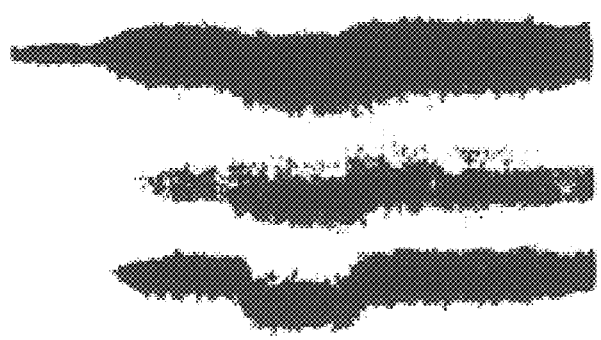

The 461-bp EagI/SmaI fragment of B3 was isolated and used to probe $8 \times 10^6$ clones of a pREP4-cloned unidirectional cDNA library from DEB-treated lymphoblastoid cells (Strathdee, C. A., et al. *Nature* 356:763–767 (1992)). Twelve cDNA clones were identified, and the 5' end of 11 were sequenced. Eight of them are apparently full-length cDNAs (FIG. 3). By restriction enzyme analysis, 1 of the 12 clones was shown to contain a deletion 3' of nucleotide 2897 and the insertion of about 250 bp there.

5'-RACE (rapid amplification of cDNA ends) was performed to characterize the 5' sequences of the candidate gene using a Clontech Marathon™ cDNA Amplification Kit according the manufacturers specifications. Briefly, first-strand synthesis was carried out with MMLV reverse transcriptase using polyT-primed RNAs prepared from cultured fibroblast, lymphoblastoid, and HeLa cells and polyA+ RNA from placenta (provided in the kit). Then, second-strand synthesis was performed with RNAseH, *E. coli* PoLI, and *E. coli* DNA ligase. The DNA ends were made blunt with T7 DNA polymerase, and adapters with overhanging ends were ligated to the cDNA. Nested PCRs then were carried out using 5' oligonucleotides from the adaptor (AP1 and AP2) and internal 3' oligonucleotides from the H1–5' sequence (BC5, GCCATCACCGGAACAGAAGGAAA; and BC11, TCTTCTGGAGAAGGTGGAACAA). Bands derived from the H1–5' sequences were identified in all four of the cDNA samples. PCR products from the 5'-RACE-amplified fibroblast cDNA was cloned into Bluescript, and the 5' ends of 12 clones were sequenced (FIG. 3).

D. Northern Blot Analysis

RNAs were prepared from cultured cells using TRIzol reagent (Gibco, BRL) according to the manufacturer's instructions. Total RNAs (30 μg) were size-separated by electrophoresis through 6.3% formaldehyde 1.2% agarose gels in 0.02 M MOPS, 0.05 M sodium acetate pH 7.0, and 0.001 M EDTA. The RNAs were transferred to Hybond-N (Amersham) in 20×SSPE and fixed to the membranes by Uv-crosslinking. Hybridizations were performed as described (Ellis, N. A., et al. *Nature Genetics* 6:394–400 (1994)).

E. Single-Strand Conformation Polymorphism (SSCP) Analysis

After first-strand synthesis, PCR was carried out with 200 ng cDNA, 5.2 pmol of each oligonucleotide primer (Table 2), 3% DMSO, 0.2 mM dNTPs (Pharmacia), 1×reaction buffer from Boehringer Mannheim, 0.25 units of Taq polymerase (Boehringer Mannheim), and 1.0 μCi of $\alpha$-$[^{32}P]$-dCTP in a total volume of 10 μl. Each reaction was overlaid with mineral oil and initially denatured for 5 min at 94° C. followed by 35 cycles of 94° C. for 1 min, 60° C. for 1 min, and 72° C. for 1 min. The last cycle was extended at 72° C. for 5 min. PCR products were diluted in 25 μl of 0.1% SDS, 10 mM EDTA and 25 μl of 95% formamide, 20 mM EDTA, 0.5% bromophenol blue, and 0.5% xylene cyanol. Two conditions for electrophoresis were carried out for each set of reactions. In one, electrophoresis of a 90 mM Tris borate, 2 mM EDTA (pH 7.5) (Gibco, BRL), 35% MDE (AT Biochem) 10% glycerol gel was performed at room temperature, cooled by fans; in the other, electrophoresis of a 90 mM Tris borate, 2 mM (Gibco, BRL), 25% MDE (AT Biochem) gel was performed at 4° C. Electrophoresis was carried out for both conditions at 40W constant power in 0.6×TBE running buffer. After electrophoresis, gels were transferred to 3MM paper and dried on a vacuum slab dryer. Autoradiography overnight with Kodak XAR5 film without intensifying screens was sufficient to detect bands.

F. DNA Sequencing of SSCP Conformers

Isolation of DNA from SSCP conformers was performed as described previously in Groden et al. (*Cell* 66:589–600 (1991); *Am. J. Hum. Genet.* 52:263–272 (1993)). Each sample was analyzed by agarose gel electrophoresis to confirm the correct size. The remainder of each sample was purified using Centricon 100 columns (Amicon) and sequenced using the dsDNA Cycle Sequencing System (Gibco, BRL) with the forward primer originally designed for SSCP analysis. Sequencing reactions were analyzed by electrophoresis through 5% denaturing polyacrylamide gels. Gels were dried and exposed to Hyperfilm-MP (Amersham) without intensifying screens.

II. Results

A. Localization of BLM to a 250-kb Interval

Figure 1B:
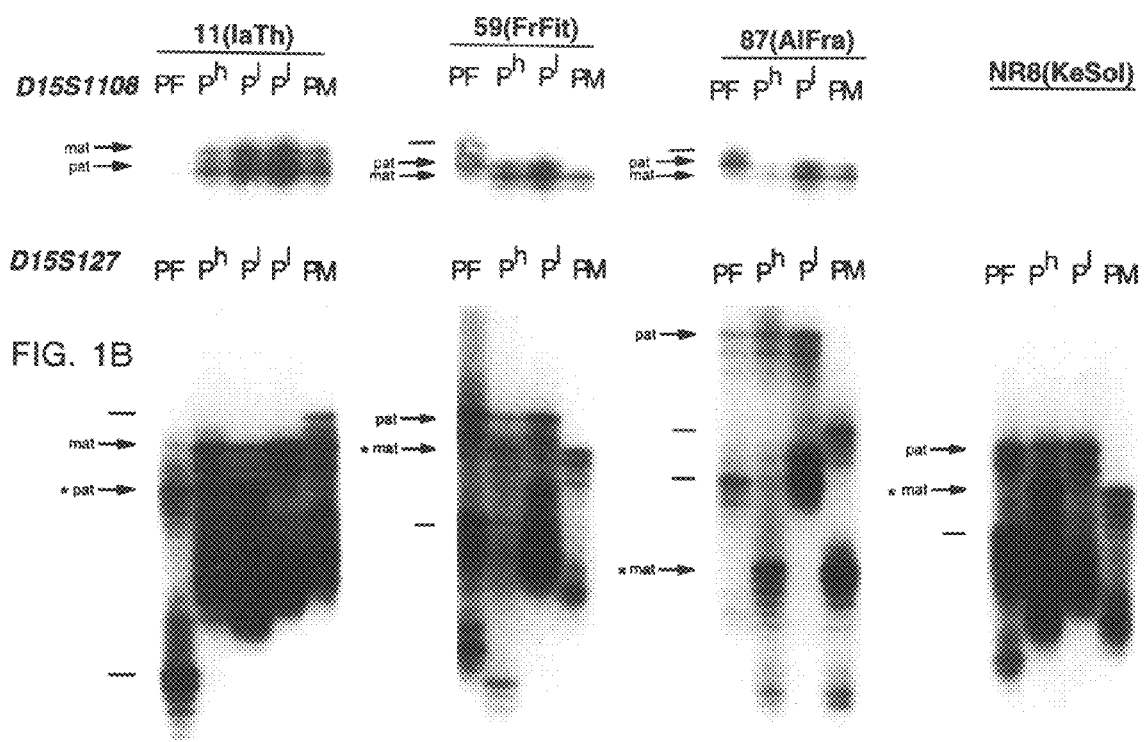
FIG. 1B represents the autoradiographic evidence showing heterozygosity proximal to BLM and reduction to homozygosity distal to BLM. The four persons of five from whom low-SCE LCLs had been established that were informative at D15S1108 or D15S127 are shown. To determine both the constitutional and the recombinant cell line genotypes, PCRs were carried out using DNA samples prepared from high-SCE cells ($P^h$) and low-SCE LCLs ($P^l$) of persons with BS as well as samples from their fathers (PF) and their mothers (PM). These persons are identified by their Bloom's Syndrome Registry designations (see German, J., and Passarge, E. Clin. Genet. 35:57–69 (1989)). Arrows point to DNA fragments amplified from the heterozygous alleles of the constitutional genotypes, pat (for paternal) and mat (for maternal). Asterisks mark alleles in the low-SCE LCLs that are lost through somatic crossing-over. Lines mark DNA fragments amplified from alleles of the parents but that were not transmitted to the offspring with BS. From one of the four persons with BS, 11 different clonal LCLs were examined; 3 of the 11 had undergone reduction to homozygosity at loci distal to BLM—as explained elsewhere ((Ellis, N. A., et al. Somatic intragenic recombination within the mutated locus BLM can correct the high-SCE phenotype of Bloom syndrome cells. Am. J. Hum. Genet., 1995, in press). Autoradiographic patterns are shown from 2 of the 11 low-SCE LCLs from 11(IaTh), one representative of cell lines in which allele losses were detected ($p^l$ sample on right) and another of cell lines in which they were not ($p^l$ sample on left).

BLM previously was localized by SCP mapping to a 1.3 cM interval bounded proximally by D15S116 and distally by four tightly linked loci D15S127, FES, D15S158, and IP15M9 (Ellis, et al., *Am. J. Hum. Genet.*, 1995, supra). The four loci are present in a 1–2 cM interval on chromosome 15 (Beckmann, et al., supra; Gyappay, et al., supra). The order of these four loci was determined by PCR analysis of clones in a 2-Mb YAC and P1 contig that encompasses BLM (Straughen, et al., supra). The four loci were oriented with respect to the telomere by finding a recombinant chromosome in a BS family in which crossing-over had occurred between BLM and IP15M9, placing IP15M9 on the distal end of the contig (FIG. 1A). Because D15S127 was the most proximal locus that was reduced to homozygosity in low-SCE LCLs, polymorphic loci in the region proximal to it were sought. There, a polymorphic locus, D15S1108, was identified that remained constitutionally heterozygous in the recombinant low-SCE LCLs, in contrast to locus D15S127 that had become homozygous in them (FIG. 1B). This shift from heterozygosity to homozygosity of markers indicated that BLM is situated in the 250-kb region between D15S1108 and D15S127.

Two genes, FES and FUR, map distal to D15S127 in this region of chromosome 15. SCP mapping thereby eliminated them as candidates for BLM. Consistent with this conclusion, an earlier mutation search in six BS LCLs had failed to uncover mutations in FUR (data not shown).

B. Isolation of a Candidate for BLM cDNAs were isolated from the 250-kb region between D15S1108 and D15S127 by direct cDNA selection using cDNA libraries from cultured fibroblasts and the T-cell line Jurkat. Libraries from these cell lines were chosen because fibroblasts and T lymphocytes from persons with BS exhibit the high-SCE phenotype, indicating that BLM is expressed in these cell types. In direct selection experiments using cosmid c905 (see FIG. 1A), an 847-bp cDNA designated 905-28 was isolated after two rounds of direct selection. It was found in less than 1 in $1 \times 10^6$ clones screened in the fibroblast library but was present in 6 of 28 selected cDNA clones, a 250,000-fold enrichment. The six cDNAs represented by 905-28 were the only selected cDNAs that by Southern analysis mapped to the BLM region and that identified non-repetitive sequences in the human genome (data not shown). The 905-28 cDNA identified single-copy sequences that are situated approximately 55 kb proximal to FUR (FIG. 1A).

The 905-28 cDNA then was used to screen a HeLa cDNA library. Twenty eight cDNAs were isolated, representing at least 15 distinct classes of overlapping clones. Each of these classes had the same sequence as the 905-28 cDNA at their 3' ends but a different length of 5' sequence. In the longest cDNA isolated, clone H1, a long reading frame was found that was open to the 5' end. Additional sequences upstream of the start of the H1 cDNA were identified by a PCR cloning method (see above). Clones extending 5' of the H1 cDNA were isolated from the HeLa library., permitting the identification of 4,437 bp of sequence, which is referred herein as the H1–5' sequence (FIG. 2).

Starting at the first in-frame ATG 74 bp from its 5' end, the H1-5, sequence encodes a 1,417 amino acid peptide with a predicted molecular weight of 159 kDa. No in-frame stop codons were present between this ATG and the 5' end of the H1–5' sequences. An extensive cDNA analysis was carried out to map the 5' end of the candidate gene. $8 \times 10^6$ LCL cDNA clones were screened by hybridization with a 5' probe. Eleven clones were isolated, and their 5' ends were sequenced (FIG. 3). In addition, 12 fibroblast clones prepared by a 5' rapid amplification of cDNA ends (RACE) technique were sequenced. Both analyses indicated that the H1–5' sequence is full-length.

The predicted peptide encoded in the H1–5' sequence was used to carry out a BLASTP search of amino acid sequence databases. The searches identified significant homologies to motifs present in the three known peptides in the RecQ subfamily of DExH box-containing helicases (FIG. 4). The amino acid identities were concentrated in the region (residues 649 to 1041) containing the seven conserved helicase domains of the human RECQL (49%), *S. cerevisiae* SGS1 (46%), and *E. coli* recQ (42%) genes. This suggests that the product of the candidate gene is a DNA helicase.

The seven helicase domains identified by their homology to RecQ constitute only the middle third of the predicted peptide. Between residues 588 and 661, amino acid identities were discovered with three short motifs present in a broad phylogenetic spectrum of RNA polymerase II largest subunits (marked by asterisks in FIG. 2). The function of these motifs is unknown. No other significant homologies were identified to amino acid sequences in databases.

The amino-acid composition of the non-helicase regions of the predicted peptide is unusual. The amino-terminal 648 residues of the peptide are rich in acidic (17%), basic (12%), and polar (34%) amino acids; 13% of the residues are serines. Similarly, the carboxy-terminal 376 residues also are rich in acidic (11%), basic (16%), and polar (30%) amino acids; and again, 14% of the residues are serines. The function of these highly charged regions is unknown.

C. RNA Expression of the Candidate Gene in Cultured Cells

Northern blot analysis was used to determine the size of the full-length transcript from the candidate gene. The H1 cDNA was hybridized to total RNAs prepared from HeLa cells, normal diploid cultured fibroblasts, and non-BS LCLs. Two RNA bands at approximately 4.5 kb were visualized on the autoradiogram (FIG. 5A). This size is consistent with the length of the longest cDNAs sequenced (FIGS. 2 and 3).

In addition, Northern blot analysis was performed using total RNAs prepared from LCLs from seven unrelated persons with BS (FIG. 5B). In three BS LCLs the quantity of RNAs identified by hybridization to the H1 cDNA was decreased in comparison to that of the control LCLs. In the other four BS LCLs the pattern of RNA mobilizes is aberrant: in one the upper band is missing, in another the lower band is missing, and in remaining two the ratio of the two RNA bands was reversed compared to that in normal cells; i.e., the intensity of the lower of the two bands was increased and the upper decreased in the BS LCLs. The RNA loading was equal in all the lanes as evidenced by hybridization with a probe for the G3PD6 (glyceraldehyde-3-phosphate-dehydrogenase) gene. These observations suggest that RNAs identified by the H1 cDNA might be destabilized in BS LCLs as result of mutations in the candidate gene (see Surdej, P., et al. *Ann. Rev. Genet.* 28:263–282 (1994)).

D. Mutations in the Candidate Gene in Persons With BS

To determine whether the candidate gene is BLM, RNAs were prepared from LCLs from 13 unrelated persons with BS and from cell lines from 4 unaffected controls. These RNAs were used to generate cDNAs for mutational analysis of the expressed sequences of the candidate gene. Sequences in these 13 BS and 4 control non-BS cDNAs were amplified in approximately 200-bp segments using PCR primers designed from the open reading frame in the H1–5' sequence (Table 2). The amplified segments were analyzed by single strand conformation polymorphism (SSCP) analysis using two conditions for electrophoresis. Novel SSCP conformers (FIG. 6) were identified, and the genetic changes underlying them were sequenced (Table 1).

Seven unique mutations were identified in 10 persons with BS (the boxed and diamond-marked nucleotides in FIG. 2), as well as four polymorphic base pairs which will not be described here. Four of the mutations introduced premature nonsense codons into the coding sequence, and three introduced amino acid substitutions (see below). One of the four chain-terminating mutations arose by a 3-bp deletion, one by a nucleotide substitution, one by a 1-bp insertion that caused a frameshift, and one by a 6-bp deletion accompanied by a 7-bp insertion that also caused a frameshift. This last mutation was detected in all four persons with Ashkenazi Jewish ancestry. The potential products encoded in these four mutant alleles are 185, 271, 515, and 739 amino acids in length, respectively, and none contains a complete set of the 7 helicase domains. Three of these mutant alleles were detected in the homozygous state, indicating that the persons inheriting them in double dose probably have no active BLM gene product in their cells. These observations are evidence that the H1–5' sequences are mutated in persons with BS, thereby proving that the candidate gene is BLM.

Finally, two putative missense mutations were identified in two persons with BS that introduced amino acid substitutions at residues conserved in RecQ helicases (residues with asterisks in FIG. 4), and one was identified that introduced an amino acid substitution of cysteine to serine in the C-terminal region of the peptide. Because the three genetic alterations could be polymorphisms and the actual BS-associated mutations could have gone undetected, analyses of the BLM gene product in vitro will be required to demonstrate whether these substitutions cause the mutant phenotype.

III. Discussion

In the present study, BLM was isolated by a positional cloning strategy. BLM first was localized by homozygosity mapping to a 2-cM interval flanking FES (German, et al., 1994, supra), a gene already mapped to chromosome band 15q26.1. A 2-Mb YAC and P1 contig encompassing FES was constructed, and closely spaced polymorphic DNA markers in the contig were identified (Straughen, et al., supra). BLM then was assigned by SCP mapping to a 250-kb interval in the contig, one bounded by the polymorphic loci D15S1108 and D15S127 (FIG. 1). A cDNA clone (905-28) was isolated by direct cDNA selection using a cosmid clone from the interval, and cDNA analysis identified the 4,437-bp H1–5' sequence (FIG. 2). This sequence encodes a putative peptide homologous to the RecQ helicases (FIG. 4). RNA transcripts 4.5-kb long were identified by Northern blot analysis (FIG. 5A), and electrophoretic abnormalities in RNAs were detected in cells from seven unrelated persons with BS, suggesting that these RNAs are derived from mutant BLM genes (FIG. 5B). Finally, RT-PCR/SSCP analysis disclosed 7 unique mutations in 10 persons with BS (Table 1; FIG. 6), 4 that are chain-terminating and 3 that are putative missense substitutions, 2 of the 3 affecting amino acid residues conserved in RecQ helicases and the third changing a cysteine to a serine.

A. SCP Mapping, a Powerful New Strategy

In a recent tabulation of the 42 inherited disease-associated genes isolated by positional cloning (Collins, F. *Nature Genetics* 9:347–350 (1995)) 19 were transmitted as autosomal dominants and 17 as X-linked recessives; however, only 5 were autosomal recessives. The reasons for the paucity of positionally cloned autosomal recessive disease-associated genes are at least twofold. First, the cloning of over half of the genes (26 of the 42 tabulated) was aided by chromosome breakpoints within or near the disease-associated gene; however, only one of these was in an autosomal recessive. Secondly, and of greater importance, the number of families transmitting rare autosomal recessive disease-associated genes generally is small, and the number of persons in sibships who would be informative in recombinational analysis also is small. Because a single investigator usually cannot obtain the numbers of families required for linkage analysis, the localization and subsequent positional cloning of rare autosomal recessive genes has lagged behind that of dominant and X-linked recessive genes.

Even when samples from numerous families have been collected and analyzed, usually the amount of positional information obtained is limited. In the case of BS, the Bloom's Syndrome Registry (German and Passarge, supra), a research resource that has provided the material for all of the inventors' recent genetical studies, made possible an extensive recombinational analysis of BLM by homozygosity mapping. This analysis permitted a minimum regional assignment of BLM to approximately 1.4 Mb (unpublished results). This size of minimum interval is typical of recombinational analysis. A search for and subsequent mutational analysis of genes from a 1.4-Mb region would have been laborious.

The problem of too little positional information in available families can be mitigated in exceptional situations in which linkage disequilibrium between the disease-associated gene and tightly-linked polymorphisms can be detected in a genetic isolate. In these cases localization of a gene to a short interval in the genome by haplotype analysis can be more exact than is possible using standard linkage analysis of family data (e.g., Kerem, B.-S., et al. *Science* 245:1073–1080 (1989); Sirugo, G., et al. *Am. J. Hum. Genet.* 50:559–566 (1992); Lehesjoki, A. E., et al. *Hum. Mol. Genet.* 2:1229–1234 (1993); Hastbacka, J., et al. *Cell* 78:1073–1087 (1994)). Linkage disequilibrium in fact was a strategy available in BS (Ellis, et al., *Am. J. Hum. Genet.*, 1994, supra), and it permitted a minimum regional assignment of BLM to the same 250-kb interval described herein (Ellis, et al., Linkage-disequilibrium mapping permits assignment of the Bloom's syndrome gene BLM to a 250-kb genomic DNA segment on chromosome 15. *Genomics*, submitted). This approach could have allowed the inventors to clone BLM. Instead, the inventors carried out SCP mapping first.

In the SCP-mapping strategy, the inventors took advantage of recombinant cell lines from BS somatic cells in which crossing-over within BLM had taken place, resulting in the correction of the mutant phenotype in their progenies (Ellis, et al., *Am. J. Hum. Genet.*, 1995, supra). After a segregational event, all polymorphic loci distal to BLM were reduced to homozygosity in half of the cases of intragenic recombination. This mapping method was preferred to linkage-disequilibrium mapping because the crossovers that permitted localization of BLM had occurred within the gene itself and fewer genotypes were required for the analysis. By genotyping polymorphic loci that flank BLM in high-SCE and low-SCE samples from only five persons with BS and their parents, the position of BLM was delimited to the short interval bounded by the marker loci D15S1108 and D15S127 (FIG. 1). With BLM assigned to such a short interval the cloning of BLM became straightforward. The first candidate gene isolated from the interval proved to be BLM.

B. Loss-of-Function Mutations at BLM

The candidate gene for BLM isolated from the interval identified by SCP mapping encodes a 1,417 amino acid peptide, previously unrecognized but homologous to RecQ helicases. Mutational analysis of the first 13 unrelated persons with BS examined permitted the identification of 7 unique mutations in 10 of them (Table 1). The fact that four of the seven mutations characterized so far result in premature termination of translation indicates that the cause of most BS is the loss of enzymatic activity of the BLM gene product. Identification of loss-of-function mutations in BLM (Table 1) is consistent with the autosomal recessive transmission of BS, and the homology of BLM and RecQ suggests that BLM has enzymatic activity. Thus, it is predicted that most BS mutations result in loss of function of BLM.

This loss of enzymatic activity is not lethal in cells, because three of the chain-terminating mutations were detected in a homozygous state. The non-lethality could result from the existence of some residual enzymatic activity in the truncated peptides; however, this seems unlikely because one of the homozygous chain-terminating mutations results in chain termination after only 185 amino acids in a person with typical BS. Alternatively, the function of BLM may not be essential for cell survival. Other factors in the cell may be able to substitute for BLM, albeit inefficiently.

In the four persons with Jewish ancestry, a 6-bp deletion/7-bp insertion at nucleotide 2,281 was identified and each of the four persons was homozygous for the mutation. Homozygosity was predictable because linkage disequilibrium had been detected in Ashkenazi Jews with BS between BLM, D15S127, and FES (Ellis, et al., *Am. J. Hum. Gen.*, 1994, supra). Thus, a person who carried this 6-bp deletion/7-bp insertion was a founder of the Ashkenazi Jewish population, and nearly all Ashkenazi Jews with BS inherit the mutation identical by descent from this common ancestor. Identification of the mutation now permits the screening of carriers in the Ashkenazim by a simple PCR test.

BS is an autosomal recessive with high penetrance and expressivity. The observation of loss-of-function mutations in BLM helps to explain these genetic characteristics. The short stature, characteristic facies, facial sun-sensitivity, hyper- and hypopigmented patches on the skin, immunodeficiency, male infertility, female subfertility, premature menopause, and the predispositions to late-onset diabetes and to neoplasia exist in virtually all groups of persons with the syndrome. The BS phenotype is similar in the Ashkenazi Jews, the Dutch, Flemish, German, Italian, Greek, Turkish, and Japanese—i.e., wherever it's been diagnosed. In addition, the elevated chromatid exchange and the hypermutability are constant cellular manifestations. No more variability in the expressivity of the mutations has been detected in persons with BS who inherit an identical mutation by descent from a common ancestor, as happens in Ashkenazi Jews with BS and in the 25% of non-Ashkenazi Jewish persons with BS whose parents are cousins, than has been detected in persons who are compound heterozygotes (German et al., 1995, supra). Nevertheless, with BLM cloned, it is possible to identify the mutations in any person with BS, and more subtle genotype-phenotype correlations now can be carried out.

C. BLM as a Putative DNA Helicase

The BLM gene product has been shown to be homologous at the amino acid level to the RecQ helicases (FIG. 4), a subfamily of DEXH box-containing DNA and RNA helicases. RecQ is an *E. coli* gene which is a member of the RecF recombination pathway (Nakayama, H., et al. *Mol. Gen. Genet.* 195:474–480 (1984)), a pathway of genes in which mutations abolish the conjugational recombination proficiency and UV-resistance of a mutant strain lacking both the RecBCD (part of exonuclease V) and the SbcB (exonuclease I) activities (Horii, Z., and Clark, A. J. *J. Mol. Biol.* 80:327–344 (1973)). RecQ has DNA-dependent ATPase and DNA helicase activities and can translocate on single-stranded DNA in a 3'-5' direction (Umezu, K., et al. *Proc. Natl. Acad. Sci. USA* 87:5363–5367 (1990)). Besides BLM, only two other recQ-like genes are known. First, SGS1 is a yeast gene in which mutations suppress the slow growth of cells carrying mutations in the TOP3 topoisomerase gene (Gangloff, S., et al. *Mol. Cel. Biol.* 14:8391–8398 (1994)). It also was isolated in a yeast two-hybrid screen through its interactions with both the yeast Top2 and Top3 topoisomerases (Gangloff, et al., supra; Watt, P. M., et al. *Cell* 81:253–260 (1995)). Secondly, REQL is a human gene isolated from HeLa cells the product of which possesses DNA-dependent ATPase, DNA helicase, and 3'-5' single-stranded DNA translocation activities (Puranam, K. L., and Blackshear, P. J. *J. Mol. Biol.* 47:29838–29845 (1994); Seki, M., et al. *Nucl. Acids Res.* 22:4566–4573 (1994)). The homology of BLM with RecQ and RECQL strongly suggests that BLM also has DNA-dependent ATPase and DNA helicase activities, and studies to investigate this have been initiated.

In addition to helicase domains, BLM contains N-terminal and C-terminal regions that are composed predominantly of charged and polar amino acid residues. The presence of non-helicase regions in BLM raises the possibility of additional enzymatic activities. The non-helicase regions could operate to provide functional specificity to BLM, e.g., by promoting interactions with other proteins, or could provide substrates for phosphorylation that might regulate BLM activity in the cell cycle.

D. A Function for BLM in DNA Replication

Some genes in the DEXH family have been implicated in DNA repair, and mutations in three of them, the XPB, XPD, and ERCC6 genes, have been identified in the human disease phenotypes xeroderma pigmentosum and Cockayne's syndrome (Weber, C. A., et al. *EMBO J.* 9:1437–1447 (1990); Frejter, W. L., et al. *Proc. Natl. Acad. Sci. USA* 89:261–265 (1992); Troelstra, C., et al. *Cell* 71:939–953 (1992); Sung, P., et al. *Nature* 365:852–855 (1993); Ma, L., et al. *Mol. Cell. Biol.* 14:4126–4134 (1994)). A universal function for the RecQ helicases, however, is not established. No abnormality in humans has been attributed to defects in RECQL. Even the cellular function of RecQ in bacteria is unclear, although it most likely participates in an aspect of post-replication recombinational repair (Luisi-DeLuca, C., et al. *Genetics* 122:269–278 (1989); Kusano, K., et al. *Proc. Natl. Acad. Sci. USA* 91:1173–1177 (1994); Tseng Y.-C., et al. *Mutation Res.* 315:1–9 (1994)). The phenotype of yeast SGSI mutants includes slow growth, poor sporulation, chromosome nondisjunction at mitosis, missegregation in meiosis (Watt, et al., supra), and an elevated recombination frequency (Gangloff, et al., supra). SGS1 is known to interact with topoisomerases II and TOP3, and therefore may function in chromosome separation, a process in which intertwined DNA strands are resolved when replication forks converge. The predicted sizes of BLM (1,417 residues) and SGS1 (1,447 residues) are similar, the two peptides have similar base-compositions outside the helicase domains, and mutations in the genes encoding them result in genomic instability. In addition, an interaction between BLM and topoisomerase II in human cells has been suggested by the observation that topoisomerase II activity is decreased in BrdU-treated BS cells (Heartlein, M. W., et al. *Exp. Cell Res.* 169:245–254 (1987)). Although these interesting similarities are inconclusive, the possible functional homology between BLM and SGS1 warrants further investigation.

In general, BLM has been implicated in the complex processes of DNA replication. Mutations in BLM have impressively pleiotropic cytogenetic and biochemical consequences. The chromosome breaks, gaps, and translocations and the high frequency of intra- and interchromosomal strand exchanges all point to a disturbance of DNA replication. In BS cells, the rate of nascent DNA chain-elongation is retarded (Hand, R., and German, J. *Proc. Natl. Acad. Sci. U.S.A.* 72:758–762 (1975); Giannelli, F., et al. *Nature* 265:466–469 (1977)), and the distribution of DNA replicational intermediates is abnormal (Lonn, U., et al. *Cancer Res.* 50:3141–3145 (1990)). Some though not all cultured BS cells exhibit increased sensitivity to DNA-damaging agents, e.g. UV radiation, mitomycin C, N-nitroso-N-ethylurea, and ethyl methanesulfonate (Krepinsky, A. B., et al. *Hum. Genet.* 50:151–156 (1979); Krepinsky, A. B., et al. *Mutation Res.* 69:357–368 (1980); Ishizaki, K., et al. *Mutation Res.* 80:213–219 (1981); Heddle, J. A., et al. (1983) Cellular sensitivity to mutagens and carcinogens in the chromosome-breakage and other cancer-prone syndromes. In Chromosome Mutation and Neoplasia, J. German, ed. (Alan R. Liss, Inc., New York), pp.203–234; Kurihara, T., et al. *Mutation Res.* 184:147–151 (1987)). Disturbances in several enzymes that participate in DNA replication, DNA repair, or both have been identified in some though, again, not all BS cell lines, including DNA ligase I (Chan, J. Y. H., et al. *Nature* 325:357–359 (1987); Willis, A. E. and Lindahl, T. *Nature* 325:355–357 (1987)), topoisomerase II in BrdU-treated BS cells (Heartlein, et al., supra), thymidylate synthetase (Shiraishi, Y., et al. *Mutation Res.* 211:273–278 (1989)), uracil DNA glycosylase (Seal, G., et al. *Proc. Natl. Acad. Sci. U.S.A.* 85:2339–2343 (1988)), N-methylpurine DNA glycosylase (Dehazya, P., and Sirover, M. A. *Cancer Res.* 46:3756–3761 (1986)), $O^6$-methylguanine methyltransferase (Kim, S., et al. *Mutation Res.* 173:141–145 (1986)), and superoxide dismutase (Nicotera, T. M., et al. *Cancer Res.* 49:5239–5243 (1989)). These investigations show that certain enzymes concerned with DNA replication and, or, repair appear to be dysregulated in BS and that cultured BS cells make variously abnormal responses to DNA-damaging agents.

The evidence that BS cells have a defect in DNA repair, however, is slight (Friedberg E. C., et al. *Adv. Rad. Biol.* 8:85–174 (1979); German, J, and Schonberg, S. (1980) Bloom syndrome. IX. Review of cytological and biochemical aspects. In Genetic and Environmental Factors in Experimental and Human Cancer, H. V. Gelboin, B. MacMahon, T. Matsushima, T. Sugimura, S. Takayama, and H. Takebe (eds.) (Japan Scientific Societies Press, Tokyo) pp 175–186). BS cells are not hypersensitive to UV or X-ray irradiation by standard assays, and no defect in a specific DNA-repair enzyme or pathway has been reported. Although the explanation for the pleiotropic effects of BS mutations still is unknown, the predicted function of BLM as a DNA helicase implies that the BS cell encounters greater difficulties than the normal in the resolution of specific DNA structures generated during DNA replication. BLM presumably is one member of an assembly of gene products that acts in a pathway to resolve these structures. The excessive rates of chromatid exchange (homologous chromatid interchange configurations at metaphase and the SCE rates) might be microscopically visible manifestations of repair processes that are activated by the mutant cell's inability to resolve the structures properly. Identification of the substrates on which BLM operates represents one of the important areas for future investigation.

IV. Conclusions

With the cloning of the BS gene and the inference that its gene product is a DNA helicase, new insight has been gained into the molecular basis of the genomic instability which is the most impressive feature of BS cells. The absence of the BLM gene product most likely destabilizes other enzymes that participate in DNA replication and repair, perhaps through direct interactions or through more general responses to DNA damage. Elucidation of the enzymatic activities of BLM, the factors with which it interacts, and the substrates on which it operates now are required in order to understand the role of BLM in the maintenance of genomic stability, and may play a role in cancer diagnosis and therapy in the population at large.

TABLE 1

Mutations identified in the candidate gene in persons with Bloom's syndrome

| Person | | | Mutation | | | | | |
|---|---|---|---|---|---|---|---|---|
| I.D.[a] | Ancestry | Cell line | Position[b] (bp) | Alteration[c] | Zygosity at BLM[d] | Kind | Codon change | Predicted peptide[e] |
| 97(AsOk) | Japanese | HG1926 | 631 | 3-bp del[f] | Homo | Nonsense | S→stop | 185 |
| 112(NaSch) | German | HG2510 | 888 | A→T | Hetero | Nonsense | K→stop | 271 |
| 93(YoYa) | Japanese | HG1626 | 1610 | 1 bp ins | Homo | Frameshift[g] | | 515 |
| 139(ViKre) | American/European | HG2231 | 2089 | A→G | Hetero | Missense | Q→R[g] | 1417 |
| 15(MaRo) | Ashkenazi Jewish | HG1514 | 2281 | 6 bp del/ 7 bp ins | Homo | Frameshift[i] | | 739 |
| 42(RaFr) | Ashkenazi Jewish | HG2522 | 2281 | 6 bp del/ 7 bp ins | Homo | Frameshift[i] | | 739 |
| 107(MyAsa) | Ashkenazi Jewish | HG2654 | 2281 | 6 bp del/ 7 bp ins | Homo | Frameshift[i] | | 739 |
| NR2(CrSpe) | Ashkenazi Jewish | HG2727 | 2281 | 6 bp del/ 7 bp ins | Homo | Frameshift[i] | | 739 |
| 92(VaBi) | Italian | HG1584 | 2596 | T→C | Homo | Missense | I→T[j] | 1417 |
| 113(DaDem) | Italian | HG1624 | 3238 | G→C | Homo | Missense | C→S[k] | 1417 |

[a]Bloom's Syndrome Registry designations. Three unrelated persons with BS were examined in whom mutations have yet to be detected: 61(DoHo), in HG2122; 30(MaKa), in HG1987; 140(DrKas), in HG1972.
[b]The nucleotide positions are as identified in the H 1-5' sequence (FIG. 2).
[c]Del, deletion; ins, insertion.
[d]Homo, homozygous; hetero, heterozygous.
[e]Number of amino acids starting from the first in-frame ATG found in the H1-5' sequence (FIG. 2).
[f]The deletion of CAA at nucleotide positions 631–633 results in a stop codon at amino acid position 186 (FIG. 2).
[g]The insertion of an A bp causes the insertion of a novel codon for K after amino acid 514 position (taken from the H 1-5' sequence, FIG. 2), and after this codon there is a stop codon.
[h]At amino acid position 672.
[i]The deletion of ATCTGA and insertion of TAGATTC causes the insertion of the novel condons for LDSR after amino acid position 736, and after these codons there is a stop codon.
[j]At amino acid position 843.
[k]At amino acid position 1055

TABLE 2

Pairs of primer sequences used for SSCP analysis of BLM.

| Name | Forward sequence[a] | Reverse sequence[a] | Product length (bp) |
|---|---|---|---|
| C1-B | GGATCCTGGTTCCGTCCGC | GAGGTTCACTGAAGGAAAAGTC | 269 |
| C1-A | CAACTAGAACGTCACTCAGCC | GAAGTCCTTGACCCTTTGCTG | 233 |
| C1-1 | GACTTTTCCTTCAGTGAACCTC | GGGATTTCTTTACAGTTGGTGTG | 186 |
| C1-2 | CCAGATTTCTTGCAGACTCCG | CTCTTACAAAGTGACTTTGGGG | 213 |
| C1-3 | CTTTAAGTACCATCAATGATTGGG | CCTCAGTCAAATCTATTTGCTCG | 227 |
| C1-4 | GAGTAAGCACTGCTCAGAAATC | GCTTAACCATTCTGAGTCATCC | 160 |
| C1-5 | CGAGCAAATAGATTTGACTGAGG | CAATACATGGAACTTTCTCAGTTG | 223 |
| C1-6 | GAAGATGCTCAGGAAAGTGAC | CGTACTAAGGCATTTTGAAGAGG | 215 |
| C1-7 | CAACTGAGAAAGTTCCATGTATTG | CACAGTCTGTGCTGGTTTCTG | 239 |
| C1-9 | CTATTCCTGATGATAAACTGAAAC | CCTTCATAGAATTCCCTGTAGG | 200 |
| C1-10 | GTGGAGATACAGGCCTGATTC | GTGTTTCAGCCCAGTTGCTAC | 244 |
| C1-11 | CAGGATTCTCTGCCACCAGG | GCAGTATGTTTATTCTGATCTTTC | 183 |
| C1-12 | CAGGAAATGTTCTCACAAGCAC | CCTTGATGGGTTGATAGGCAG | 203 |
| C1-13 | CAGCCAGCAAATCTTCCACAG | CGCTCATGTTTCAGATTTCTGG | 204 |
| C1-14 | GAATTATACTGACAAGTCAGCAC | GATCTACGATAAGTGATCTCAAG | 295 |
| C1-15 | CTCCTGGGGTCACTGTTGTC | GAGTCTGTTACTTGCACAGATC | 211 |
| C1-16 | CAATCATAAAACTTCTATATGTCAC | GCCATCACCGGAACAGAAGG | 207 |
| C1-17 | GTGGGGACATGATTTTCGTCAAG | GATTATGTCTGTTAAAGCTCATG | 175 |
| C1-18 | GACATCCTGACTCAGCTGAAG | CGTGTCAGCCATGGTGTCAC | 203 |
| C1-19 | GCACCACCCATATGATTCAGG | CAGATAACCTGACAGCCATCC | 179 |
| C1-20 | GATGAAGTGCAGCAGAAGTGG | CAGTCTGGTCACATCATGATAG | 221 |
| C1-21 | GCAGAGCTGGAAGAGATGGG | GCTGTATTCTCCTGCATTCCG | 188 |
| C1-22 | GTATAGCATGGTACATTACTGTG | CCTTGTGATGAACTATGTTCTTG | 228 |
| C1-23 | GACTGACGATGTGAAAAGTATTG | CCAAAATCTTGTCAAGTATCAGC | 235 |
| C1-24 | CCAGTCAGGTATATTTGGAAAAG | GGAATTTTCTGTTTCCATAAAGTC | 206 |
| C1-25 | CGATCGCTTATGTGATGCTCG | CAAGCTTCTTGAGAGTGACGG | 248 |
| C1-26 | GAACTTACAGAAGTCTGCAAATC | GATGTCCATTCAGAGTATTTCTG | 208 |
| C1-27 | GGTGTTACTGAAGACAAACTGG | GGGTATTTCCTCGTCAAGCTC | 168 |
| C1-28 | GGATAAGCCTGTCCAGCAGC | CCTAGATATCTTTCTACATGTGG | 214 |
| C1-29 | GCTTCCAGTGGTTCCAAGGC | GTTATGAGAATGCATATGAAGGC | 204 |
| C1-30 | CTCAAGCGACATCAGGAGCC | CAAGAATAACAGCTTTATAGTCAC | 178 |

[a]5' to 3'

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. An isolated protein having the amino acid sequence of SEQ ID NO: 78.

2. An isolated gene product encoded by a nucleic acid containing at least one mutation that results in expression of said gene product in a Bloom's syndrome patient, said nucleic acid corresponding to a mutated form of nucleic acid encoding the amino acid sequence contained in SEQ ID NO: 78, wherein said mutation is characterized by: (i) a deletion of nucleotides 631–633 of SEQ ID NO: 72; (ii) a substitution of A with T at nucleotide 888 of SEQ ID NO: 72; (iii) an insertion of A after nucleotide 1610 of SEQ ID NO: 72; (iv) a substitution of A with G at nucleotide 2089 of SEQ ID NO: 72; (v) a replacement of nucleotides ATCTGA at position 2281–2286 of SEQ ID NO: 72 with nucleotides TAGATTC; (vi) a substitution of T with C at nucleotide 2596 of SEQ ID NO: 72; or (vii) a substitution of G with C at nucleotide 3238 of SEQ ID NO: 72.

3. The gene product of claim 2, wherein said mutation is characterized by a deletion of nucleotides 631–633 of SEQ ID NO: 72.

4. The gene product of claim 2, wherein said mutation is characterized by a substitution of A with T at nucleotide 888 of SEQ ID NO: 72.

5. The gene product of claim 2, wherein said mutation is characterized by an insertion of A after nucleotide 1610 of SEQ ID NO: 72.

6. The gene product of claim 2, wherein said mutation is characterized by a substitution of A with G at nucleotide 2089 of SEQ ID NO: 72.

7. The gene product of claim 2, wherein said mutation is characterized by a replacement of nucleotides ATCTGA at position 2281–2286 of SEQ ID NO: 72 with nucleotides TAGATTC.

8. The gene product of claim 2, wherein said mutation is characterized by a substitution of T with C at nucleotide 2596 of SEQ ID NO: 72.

9. The gene product of claim 2, wherein said mutation is characterized by a substitution of G with C at nucleotide 3238 of SEQ ID NO: 72.

* * * * *

SEQUENCE LISTING (1) GENERAL INFORMATION:

(iii) NUMBER OF SEQUENCES: 78

(2) INFORMATION FOR SEQ ID NO:1:

(i) SEQUENCE CHARACTERISTICS:
      (A) LENGTH: 19
      (B) TYPE: NUCLEIC ACID
      (C) STRANDEDNESS: SINGLE
      (D) TOPOLOGY: LINEAR (ii) MOLECULE TYPE:
      (A) DESCRIPTION: OTHER NUCLEIC ACID (iii) HYPOTHETICAL: YES (iv) ANTI-SENSE: NO (xi) SEQUENCE DESCRIPTION: SEQ ID NO: 1:

GGTGGCGACG ACTCCTGGA    19

(2) INFORMATION FOR SEQ ID NO:2:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 2:

ACCAGACCAA CTGGTAATG                                           19

(2) INFORMATION FOR SEQ ID NO:3:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 3:

ATGGTAGCGA CCGGCGCTCA                                          20

(2) INFORMATION FOR SEQ ID NO:4:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 4:

CCGTCAGTAT CGGCGGAATT                                          20

(2) INFORMATION FOR SEQ ID NO:5:

```
    (i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 5:

TTGTGGTGTT GGGTAGAGGT T                                              21

(2) INFORMATION FOR SEQ ID NO:6:

(i) SEQUENCE CHARACTERISTICS:
        (A) LENGTH: 15
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 6:

GCCGCCGGCA CCAAC                                                     15

(2) INFORMATION FOR SEQ ID NO:7:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 7:

CCTCAGTCAA ATCTATNTGC TC                                             22

(2) INFORMATION FOR SEQ ID NO:8:
```

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 8:

GCCATCACCG GAACAGAAGG AAA                                              23

(2) INFORMATION FOR SEQ ID NO:9:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 9:

TCTTCTGGAG GAGGTGGAAC AA                                               22

(2) INFORMATION FOR SEQ ID NO:10:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 10:

GGATCCTGGT TCCGTCCGC                                                   19

(2) INFORMATION FOR SEQ ID NO:11:

(i) SEQUENCE CHARACTERISTICS:

```
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 11:

CAACTAGAAC GTCACTCAGC C                                              21

(2) INFORMATION FOR SEQ ID NO:12:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 12:

GACTTTTCCT TCAGTGAACC TC                                             22

(2) INFORMATION FOR SEQ ID NO:13:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 13:

CCAGATTTCT TGCAGACTCC G                                              21

(2) INFORMATION FOR SEQ ID NO:14:

(i) SEQUENCE CHARACTERISTICS:
        (A) LENGTH: 24
```

```
        (B) TYPE:  NUCLEIC ACID
        (C) STRANDEDNESS:  SINGLE
        (D) TOPOLOGY:  LINEAR (ii) MOLECULE TYPE:
        (A) DESCRIPTION:  OTHER NUCLEIC ACID (iii) HYPOTHETICAL:  YES (iv) ANTI-SENSE:  NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:  SEQ ID NO: 14:

CTTTAAGTAC CATCAATGAT TGGG                                              24

(2) INFORMATION FOR SEQ ID NO:15:

(i) SEQUENCE CHARACTERISTICS:
        (A) LENGTH: 22
        (B) TYPE:  NUCLEIC ACID
        (C) STRANDEDNESS:  SINGLE
        (D) TOPOLOGY:  LINEAR (ii) MOLECULE TYPE:
        (A) DESCRIPTION:  OTHER NUCLEIC ACID (iii) HYPOTHETICAL:  YES (iv) ANTI-SENSE:  NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:  SEQ ID NO: 15:

GAGTAAGCAC TGCTCAGAAA TC                                                22

(2) INFORMATION FOR SEQ ID NO:16:

(i) SEQUENCE CHARACTERISTICS:
        (A) LENGTH: 23
        (B) TYPE:  NUCLEIC ACID
        (C) STRANDEDNESS:  SINGLE
        (D) TOPOLOGY:  LINEAR (ii) MOLECULE TYPE:
        (A) DESCRIPTION:  OTHER NUCLEIC ACID (iii) HYPOTHETICAL:  YES (iv) ANTI-SENSE:  NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:  SEQ ID NO: 16:

CGAGCAAATA GATTTGACTG AGG                                               23

(2) INFORMATION FOR SEQ ID NO:17:

(i) SEQUENCE CHARACTERISTICS:
        (A) LENGTH: 21
        (B) TYPE:  NUCLEIC ACID
```

```
            (C) STRANDEDNESS:  SINGLE
            (D) TOPOLOGY:  LINEAR (ii) MOLECULE TYPE:
            (A) DESCRIPTION:  OTHER NUCLEIC ACID (iii) HYPOTHETICAL:  YES (iv) ANTI-SENSE:  NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION:  SEQ ID NO: 17:

GAAGATGCTC AGGAAAGTGA C                                              21

(2) INFORMATION FOR SEQ ID NO:18:

(i) SEQUENCE CHARACTERISTICS:
            (A) LENGTH:  24
            (B) TYPE:  NUCLEIC ACID
            (C) STRANDEDNESS:  SINGLE
            (D) TOPOLOGY:  LINEAR (ii) MOLECULE TYPE:
            (A) DESCRIPTION:  OTHER NUCLEIC ACID (iii) HYPOTHETICAL:  YES (iv) ANTI-SENSE:  NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION:  SEQ ID NO: 18:

CAACTGAGAA AGTTCCATGT ATTG                                           24

(2) INFORMATION FOR SEQ ID NO:19:

(i) SEQUENCE CHARACTERISTICS:
            (A) LENGTH:  24
            (B) TYPE:  NUCLEIC ACID
            (C) STRANDEDNESS:  SINGLE
            (D) TOPOLOGY:  LINEAR (ii) MOLECULE TYPE:
            (A) DESCRIPTION:  OTHER NUCLEIC ACID (iii) HYPOTHETICAL:  YES (iv) ANTI-SENSE:  NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION:  SEQ ID NO: 19:

CTATTCCTGA TGATAAACTG AAAC                                           24

(2) INFORMATION FOR SEQ ID NO:20:

(i) SEQUENCE CHARACTERISTICS:
            (A) LENGTH:  21
            (B) TYPE:  NUCLEIC ACID
            (C) STRANDEDNESS:  SINGLE
```

```
            (D) TOPOLOGY:  LINEAR (ii) MOLECULE TYPE:
            (A) DESCRIPTION:  OTHER NUCLEIC ACID (iii) HYPOTHETICAL:  YES (iv) ANTI-SENSE:  NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION:  SEQ ID NO: 20:

GTGGAGATAC AGGCCTGATT C                                                  21

(2) INFORMATION FOR SEQ ID NO:21:

(i) SEQUENCE CHARACTERISTICS:
            (A) LENGTH: 20
            (B) TYPE:  NUCLEIC ACID
            (C) STRANDEDNESS:  SINGLE
            (D) TOPOLOGY:  LINEAR (ii) MOLECULE TYPE:
            (A) DESCRIPTION:  OTHER NUCLEIC ACID (iii) HYPOTHETICAL:  YES (iv) ANTI-SENSE:  NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION:  SEQ ID NO: 21:

CAGGATTCTC TGCCACCAGG                                                    20

(2) INFORMATION FOR SEQ ID NO:22:

(i) SEQUENCE CHARACTERISTICS:
            (A) LENGTH: 22
            (B) TYPE:  NUCLEIC ACID
            (C) STRANDEDNESS:  SINGLE
            (D) TOPOLOGY:  LINEAR (ii) MOLECULE TYPE:
            (A) DESCRIPTION:  OTHER NUCLEIC ACID (iii) HYPOTHETICAL:  YES (iv) ANTI-SENSE:  NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION:  SEQ ID NO: 22:

CAGGAAATGT TCTCACAAGC AC                                                 22

(2) INFORMATION FOR SEQ ID NO:23:

(i) SEQUENCE CHARACTERISTICS:
            (A) LENGTH: 21
            (B) TYPE:  NUCLEIC ACID
            (C) STRANDEDNESS:  SINGLE
            (D) TOPOLOGY:  LINEAR
```

(ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 23:

CAGCCAGCAA ATCTTCCACA G                                              21

(2) INFORMATION FOR SEQ ID NO:24:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 24:

GAATTATACT GACAAGTCAG CAC                                            23

(2) INFORMATION FOR SEQ ID NO:25:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 25:

CTCCTGGGGT CACTGTTGTC                                                20

(2) INFORMATION FOR SEQ ID NO:26:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 26:

GAGGTTCACT GAAGGAAAAG TC                                              22

(2) INFORMATION FOR SEQ ID NO:27:

(i) SEQUENCE CHARACTERISTICS:
            (A) LENGTH: 21
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 27:

GAAGTCCTTG ACCCTTTGCT G                                               21

(2) INFORMATION FOR SEQ ID NO:28:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 28:

GGGATTTCTT TACAGTTGGT GTG                                             23

(2) INFORMATION FOR SEQ ID NO:29:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (ii) MOLECULE TYPE:

(A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 29:

CTCTTACAAA GTGACTTTGG GG                                            22

(2) INFORMATION FOR SEQ ID NO:30:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 30:

CCTCAGTCAA ATCTATTTGC TCG                                           23

(2) INFORMATION FOR SEQ ID NO:31:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 31:

GCTTAACCAT TCTGAGTCAT CC                                            22

(2) INFORMATION FOR SEQ ID NO:32:

(i) SEQUENCE CHARACTERISTICS:
            (A) LENGTH: 24
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
              (A) NAME/KEY:
              (B) LOCATION:
              (C) IDENTIFICATION METHOD:
              (D) OTHER INFORMATION:

(xi) SEQUENCE DESCRIPTION: SEQ ID NO: 32:

CAATACATGG AACTTTCTCA GTTG                                                    24

(2) INFORMATION FOR SEQ ID NO:33:

(i) SEQUENCE CHARACTERISTICS:
              (A) LENGTH: 23
              (B) TYPE: NUCLEIC ACID
              (C) STRANDEDNESS: SINGLE
              (D) TOPOLOGY: LINEAR (ii) MOLECULE TYPE:
              (A) DESCRIPTION: OTHER NUCLEIC ACID (iii) HYPOTHETICAL: YES (iv) ANTI-SENSE: NO (ix) FEATURE:
              (A) NAME/KEY:
              (B) LOCATION:
              (C) IDENTIFICATION METHOD:
              (D) OTHER INFORMATION:

(xi) SEQUENCE DESCRIPTION: SEQ ID NO: 33:

CGTACTAAGG CATTTTGAAG AGG                                                     23

(2) INFORMATION FOR SEQ ID NO:34:

(i) SEQUENCE CHARACTERISTICS:
              (A) LENGTH: 21
              (B) TYPE: NUCLEIC ACID
              (C) STRANDEDNESS: SINGLE
              (D) TOPOLOGY: LINEAR (ii) MOLECULE TYPE:
              (A) DESCRIPTION: OTHER NUCLEIC ACID (iii) HYPOTHETICAL: YES (iv) ANTI-SENSE: NO (ix) FEATURE:
              (A) NAME/KEY:
              (B) LOCATION:
              (C) IDENTIFICATION METHOD:
              (D) OTHER INFORMATION:

(xi) SEQUENCE DESCRIPTION: SEQ ID NO: 34:

CACAGTCTGT GCTGGTTTCT G                                                       21

(2) INFORMATION FOR SEQ ID NO:35:

(i) SEQUENCE CHARACTERISTICS:
              (A) LENGTH: 22
              (B) TYPE: NUCLEIC ACID
              (C) STRANDEDNESS: SINGLE
              (D) TOPOLOGY: LINEAR (ii) MOLECULE TYPE:
              (A) DESCRIPTION: OTHER NUCLEIC ACID (iii) HYPOTHETICAL: YES (iv) ANTI-SENSE: NO (ix) FEATURE:
             (A) NAME/KEY:
             (B) LOCATION:
             (C) IDENTIFICATION METHOD:
             (D) OTHER INFORMATION:

(xi) SEQUENCE DESCRIPTION: SEQ ID NO: 35:

CCTTCATAGA ATTCCCTGTA GG                                                    22

(2) INFORMATION FOR SEQ ID NO:36:

(i) SEQUENCE CHARACTERISTICS:
             (A) LENGTH: 21
             (B) TYPE: NUCLEIC ACID
             (C) STRANDEDNESS: SINGLE
             (D) TOPOLOGY: LINEAR (ii) MOLECULE TYPE:
             (A) DESCRIPTION: OTHER NUCLEIC ACID (iii) HYPOTHETICAL: YES (iv) ANTI-SENSE: NO (ix) FEATURE:
             (A) NAME/KEY:
             (B) LOCATION:
             (C) IDENTIFICATION METHOD:
             (D) OTHER INFORMATION:

(xi) SEQUENCE DESCRIPTION: SEQ ID NO: 36:

GTGTTTCAGC CCAGTTGCTA C                                                     21

(2) INFORMATION FOR SEQ ID NO:37:

(i) SEQUENCE CHARACTERISTICS:
             (A) LENGTH: 24
             (B) TYPE: NUCLEIC ACID
             (C) STRANDEDNESS: SINGLE
             (D) TOPOLOGY: LINEAR (ii) MOLECULE TYPE:
             (A) DESCRIPTION: OTHER NUCLEIC ACID (iii) HYPOTHETICAL: YES (iv) ANTI-SENSE: NO (ix) FEATURE:
             (A) NAME/KEY:
             (B) LOCATION:
             (C) IDENTIFICATION METHOD:
             (D) OTHER INFORMATION:

(xi) SEQUENCE DESCRIPTION: SEQ ID NO: 37:

GCAGTATGTT TATTCTGATC TTTC                                                  24

(2) INFORMATION FOR SEQ ID NO:38:

(i) SEQUENCE CHARACTERISTICS:
             (A) LENGTH: 21
             (B) TYPE: NUCLEIC ACID
             (C) STRANDEDNESS: SINGLE
             (D) TOPOLOGY: LINEAR (ii) MOLECULE TYPE:
             (A) DESCRIPTION: OTHER NUCLEIC ACID (iii) HYPOTHETICAL: YES (iv) ANTI-SENSE:  NO (ix) FEATURE:
              (A) NAME/KEY:
              (B) LOCATION:
              (C) IDENTIFICATION METHOD:
              (D) OTHER INFORMATION:

(xi) SEQUENCE DESCRIPTION:  SEQ ID NO: 38:

CCTTGATGGG TTGATAGGCA G                                             21

(2) INFORMATION FOR SEQ ID NO:39:

(i) SEQUENCE CHARACTERISTICS:
              (A) LENGTH: 22
              (B) TYPE:  NUCLEIC ACID
              (C) STRANDEDNESS:  SINGLE
              (D) TOPOLOGY:  LINEAR (ii) MOLECULE TYPE:
              (A) DESCRIPTION:  OTHER NUCLEIC ACID (iii) HYPOTHETICAL:  YES (iv) ANTI-SENSE:  NO (ix) FEATURE:
              (A) NAME/KEY:
              (B) LOCATION:
              (C) IDENTIFICATION METHOD:
              (D) OTHER INFORMATION:

(xi) SEQUENCE DESCRIPTION:  SEQ ID NO: 39:

CGCTCATGTT TCAGATTTCT GG                                            22

(2) INFORMATION FOR SEQ ID NO:40:

(i) SEQUENCE CHARACTERISTICS:
              (A) LENGTH: 23
              (B) TYPE:  NUCLEIC ACID
              (C) STRANDEDNESS:  SINGLE
              (D) TOPOLOGY:  LINEAR (ii) MOLECULE TYPE:
              (A) DESCRIPTION:  OTHER NUCLEIC ACID (iii) HYPOTHETICAL:  YES (iv) ANTI-SENSE:  NO (ix) FEATURE:
              (A) NAME/KEY:
              (B) LOCATION:
              (C) IDENTIFICATION METHOD:
              (D) OTHER INFORMATION:

(xi) SEQUENCE DESCRIPTION:  SEQ ID NO: 40:

GATCTACGAT AAGTGATCTC AAG                                           23

(2) INFORMATION FOR SEQ ID NO:41:

(i) SEQUENCE CHARACTERISTICS:
              (A) LENGTH: 22
              (B) TYPE:  NUCLEIC ACID
              (C) STRANDEDNESS:  SINGLE
              (D) TOPOLOGY:  LINEAR (ii) MOLECULE TYPE:
              (A) DESCRIPTION:  OTHER NUCLEIC ACID (iii) HYPOTHETICAL:  YES

```
        (iv) ANTI-SENSE:  NO (ix) FEATURE:
             (A) NAME/KEY:
             (B) LOCATION:
             (C) IDENTIFICATION METHOD:
             (D) OTHER INFORMATION:

(xi) SEQUENCE DESCRIPTION:  SEQ ID NO: 41:

GAGTCTGTTA CTTGCACAGA TC                                                      22

(2) INFORMATION FOR SEQ ID NO:42:

(i) SEQUENCE CHARACTERISTICS:
             (A) LENGTH: 25
             (B) TYPE:  NUCLEIC ACID
             (C) STRANDEDNESS:  SINGLE
             (D) TOPOLOGY:  LINEAR (ii) MOLECULE TYPE:
             (A) DESCRIPTION:  OTHER NUCLEIC ACID (iii) HYPOTHETICAL:  YES (iv) ANTI-SENSE:  NO (ix) FEATURE:
             (A) NAME/KEY:
             (B) LOCATION:
             (C) IDENTIFICATION METHOD:
             (D) OTHER INFORMATION:

(xi) SEQUENCE DESCRIPTION:  SEQ ID NO: 42:

CAATCATAAA ACTTCTATAT GTCAC                                                   25

(2) INFORMATION FOR SEQ ID NO:43:

(i) SEQUENCE CHARACTERISTICS:
             (A) LENGTH: 23
             (B) TYPE:  NUCLEIC ACID
             (C) STRANDEDNESS:  SINGLE
             (D) TOPOLOGY:  LINEAR (ii) MOLECULE TYPE:
             (A) DESCRIPTION:  OTHER NUCLEIC ACID (iii) HYPOTHETICAL:  YES (iv) ANTI-SENSE:  NO (ix) FEATURE:
             (A) NAME/KEY:
             (B) LOCATION:
             (C) IDENTIFICATION METHOD:
             (D) OTHER INFORMATION:

(xi) SEQUENCE DESCRIPTION:  SEQ ID NO: 43:

GTGGGGACAT GATTTTCGTC AAG                                                     23

(2) INFORMATION FOR SEQ ID NO:44:

(i) SEQUENCE CHARACTERISTICS:
             (A) LENGTH: 21
             (B) TYPE:  NUCLEIC ACID
             (C) STRANDEDNESS:  SINGLE
             (D) TOPOLOGY:  LINEAR (ii) MOLECULE TYPE:
             (A) DESCRIPTION:  OTHER NUCLEIC ACID (iii) HYPOTHETICAL:  YES (iv) ANTI-SENSE:  NO
```

(ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 44:

GACATCCTGA CTCAGCTGAA G                                    21

(2) INFORMATION FOR SEQ ID NO:45:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 45:

GCACCACCCA TATGATTCAG G                                    21

(2) INFORMATION FOR SEQ ID NO:46:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 46:

GATGAAGTGC AGCAGAAGTG G                                    21

(2) INFORMATION FOR SEQ ID NO:47:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 47:

GCAGAGCTGG AAGAGATGGG                                            20

(2) INFORMATION FOR SEQ ID NO:48:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 48:

GTATAGCATG GTACATTACT GTG                                        23

(2) INFORMATION FOR SEQ ID NO:49:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 49:

GACTGACGAT GTGAAAAGTA TTG                                        23

(2) INFORMATION FOR SEQ ID NO:50:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:

(A) NAME/KEY:
            (B) LOCATION:
            (C) IDENTIFICATION METHOD:
            (D) OTHER INFORMATION:

(xi) SEQUENCE DESCRIPTION: SEQ ID NO: 50:

CCAGTCAGGT ATATTTGGAA AAG                                          23

(2) INFORMATION FOR SEQ ID NO:51:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 51:

CGATCGCTTA TGTGATGCTC G                                            21

(2) INFORMATION FOR SEQ ID NO:52:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 52:

GAACTTACAG AAGTCTGCAA ATC                                          23

(2) INFORMATION FOR SEQ ID NO:53:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:

(B) LOCATION:
            (C) IDENTIFICATION METHOD:
            (D) OTHER INFORMATION:

(xi) SEQUENCE DESCRIPTION: SEQ ID NO: 53:

GGTGTTACTG AAGACAAACT GG                                                              22

(2) INFORMATION FOR SEQ ID NO:54:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 54:

GGATAAGCCT GTCCAGCAGC                                                                 20

(2) INFORMATION FOR SEQ ID NO:55:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 55:

GCTTCCAGTG GTTCCAAGGC                                                                 20

(2) INFORMATION FOR SEQ ID NO:56:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:

(C) IDENTIFICATION METHOD:
            (D) OTHER INFORMATION:

(xi) SEQUENCE DESCRIPTION: SEQ ID NO: 56:

CTCAAGCGAC ATCAGGAGCC                                           20

(2) INFORMATION FOR SEQ ID NO:57:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 57:

GCCATCACCG GAACAGAAGG                                           20

(2) INFORMATION FOR SEQ ID NO:58:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 58:

GATTATGTCT GTTAAAGCTC ATG                                       23

(2) INFORMATION FOR SEQ ID NO:59:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:

(D) OTHER INFORMATION:

(xi) SEQUENCE DESCRIPTION: SEQ ID NO: 59:

CGTGTCAGCC ATGGTGTCAC                                               20

(2) INFORMATION FOR SEQ ID NO:60:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 60:

CAGATAACCT GACAGCCATC C                                             21

(2) INFORMATION FOR SEQ ID NO:61:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 61:

CAGTCTGGTC ACATCATGAT AG                                            22

(2) INFORMATION FOR SEQ ID NO:62:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 62:

GCTGTATTCT CCTGCATTCC G                                                    21

(2) INFORMATION FOR SEQ ID NO:63:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 63:

CCTTGTGATG AACTATGTTC TTG                                                  23

(2) INFORMATION FOR SEQ ID NO:64:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 64:

CCAAAATCTT GTCAAGTATC AGC                                                  23

(2) INFORMATION FOR SEQ ID NO:65:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 65:

GGAATTTTCT GTTTCCATAA AGTC                                                  24

(2) INFORMATION FOR SEQ ID NO:66:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 66:

CAAGCTTCTT GAGAGTGACG G                                                     21

(2) INFORMATION FOR SEQ ID NO:67:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 67:

GATGTCCATT CAGAGTATTT CTG                                                   23

(2) INFORMATION FOR SEQ ID NO:68:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 68:

```
GGGTATTTCC TCGTCAAGCT C                                                   21

(2) INFORMATION FOR SEQ ID NO:69:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 69:

CCTAGATATC TTTCTACATG TGG                                                 23

(2) INFORMATION FOR SEQ ID NO:70:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 70:

GTTATGAGAA TGCATATGAA GGC                                                 23

(2) INFORMATION FOR SEQ ID NO:71:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 71:
```

CAAGAATAAC AGCTTTATAG TCAC                                                24

(2) INFORMATION FOR SEQ ID NO:72:

(i) SEQUENCE CHARACTERISTICS:
        (A) LENGTH: 4437
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 72:

```
GCGCGGCGGC CGTGGTTGCG GCGCGGGAAG TTTGGATCCT GGTTCCGTCC GCTAGGAGTC    60

TGCGTGCGAG GATTATGGCT GCTGTTCCTC AAAATAATCT ACAGGAGCAA CTAGAACGTC   120

ACTCAGCCAG AACACTTAAT AATAAATTAA GTCTTTCAAA ACCAAAATTT TCAGGTTTCA   180

CTTTTAAAAA GAAAACATCT TCAGATAACA ATGTATCTGT AACTAATGTG TCAGTAGCAA   240

AAACACCTGT ATTAAGAAAT AAAGATGTTA ATGTTACCGA AGACTTTTCC TTCAGTGAAC   300

CTCTACCCAA CACCACAAAT CAGCAAAGGG TCAAGGACTT CTTTAAAAAT GCTCCAGCAG   360

GACAGGAAAC ACAGAGAGGT GGATCAAAAT CATTATTGCC AGATTTCTTG CAGACTCCGA   420

AGGAAGTTGT ATGCACTACC CAAAACACAC CAACTGTAAA GAAATCCCGG GATACTGCTC   480

TCAAGAAATT AGAATTTAGT TCTTCACCAG ATTCTTTAAG TACCATCAAT GATTGGGATG   540

ATATGGATGA CTTTGATACT TCTGAGACTT CAAAATCATT TGTTACACCA CCCCAAAGTC   600

ACTTTGTAAG AGTAAGCACT GCTCAGAAAT CAAAAAAGGG TAAGAGAAAC TTTTTTAAAG   660

CACAGCTTTA TAACAAAAC ACAGTAAAGA CTGATTTGCC TCCACCCTCC TCTGAAAGCG   720

AGCAAATAGA TTTGACTGAG GAACAGAAGG ATGACTCAGA ATGGTTAAGC AGCGATGTGA   780

TTTGCATCGA TGATGGCCCC ATTGCTGAAG TGCATATAAA TGAAGATGCT CAGGAAAGTG   840

ACTCTCTGAA AACTCATTTG GAAGATGAAA GAGATAATAG CGAAAAGAAG AAGAATTTGG   900

AAGAAGCTGA ATTACATTCA ACTGAGAAAG TTCCATGTAT TGAATTTGAT GATGATGATT   960

ATGATACGGA TTTTGTTCCA CCTTCTCCAG AAGAAATTAT TTCTGCTTCT TCTTCCTCTT  1020

CAAAATGCCT TACTACGTTA AAGGACCTTG ACACATCTGA CAGAAAAGAG GATGTTCTTA  1080

GCACATCAAA AGATCTTTTG TCAAAACCTG AGAAAATGAG TATGCAGGAG CTGAATCCAG  1140

AAACCAGCAC AGACTGTGAC GCTAGACAGA TAAGTTTACA GCAGCAGCTT ATTCATGTGA  1200

TGGAGCACAT CTGTAAATTA ATTGATACTA TTCCTGATGA TAAACTGAAA CTTTTGGATT  1260

GTGGGAACGA ACTGCTTCAG CAGCGGAACA TAAGAAGGAA ACTTCTAACG GAAGTAGATT  1320

TTAATAAAAG TGATGCCAGT CTTCTTGGCT CATTGTGGAG ATACAGGCCT GATTCACTTG  1380

ATGGCCCTAT GGAGGGTGAT TCCTGCCCTA CAGGGAATTC TATGAAGGAG TTAAATTTTT  1440

CACACCTTCC CTCAAATTCT GTTTCTCCTG GGGACTGTTT ACTGACTACC ACCCTAGGAA  1500

AGACAGGATT CTCTGCCACC AGGAAGAATC TTTTTGAAAG GCCTTTATTC AATACCCATT  1560

TACAGAAGTC CTTTGTAAGT AGCAACTGGG CTGAAACACC AAGACTAGGA AAAAAAAATG  1620
```

-continued

```
AAAGCTCTTA TTTCCCAGGA AATGTTCTCA CAAGCACTGC TGTGAAAGAT CAGAATAAAC    1680

ATACTGCTTC AATAAATGAC TTAGAAAGAG AAACCCAACC TTCCTATGAT ATTGATAATT    1740

TTGACATAGA TGACTTTGAT GATGATGATG ACTGGGAAGA CATAATGCAT AATTTAGCAG    1800

CCAGCAAATC TTCCACAGCT GCCTATCAAC CCATCAAGGA AGGTCGGCCA ATTAAATCAG    1860

TATCAGAAAG ACTTTCCTCA GCCAAGACAG ACTGTCTTCC AGTGTCATCT ACTGCTCAAA    1920

ATATAAACTT CTCAGAGTCA ATTCAGAATT ATACTGACAA GTCAGCACAA AATTTAGCAT    1980

CCAGAAATCT GAAACATGAG CGTTTCCAAA GTCTTAGTTT TCCTCATACA AAGGAAATGA    2040

TGAAGATTTT TCATAAAAAA TTTGGCCTGC ATAATTTTAG AACTAATCAG CTAGAGGCGA    2100

TCAATGCTGC ACTGCTTGGT GAAGACTGTT TTATCCTGAT GCCGACTGGA GGTGGTAAGA    2160

GTTTGTGTTA CCAGCTCCCT GCCTGTGTTT CTCCTGGGGT CACTGTTGTC ATTTCTCCCT    2220

TGAGATCACT TATCGTAGAT CAAGTCCAAA AGCTGACTTC CTTGGATATT CCAGCTACAT    2280

ATCTGACAGG TGATAAGACT GACTCAGAAG CTACAAATAT TTACCTCCAG TTATCAAAAA    2340

AAGACCCAAT CATAAAACTT CTATATGTCA CTCCAGAAAA GATCTGTGCA AGTAACAGAC    2400

TCATTTCTAC TCTGGAGAAT CTCTATGAGA GGAAGCTCTT GGCACGTTTT GTTATTGATG    2460

AAGCACATTG TGTCAGTCAG TGGGGACATG ATTTTCGTCA AGATTACAAA GAATGAATA     2520

TGCTTCGCCA GAAGTTTCCT TCTGTTCCGG TGATGGCTCT TACGGCCACA GCTAATCCCA    2580

GGGTACAGAA GGACATCCTG ACTCAGCTGA AGATTCTCAG ACCTCAGGTG TTTAGCATGA    2640

GCTTTAACAG ACATAATCTG AAATACTATG TATTACCGAA AAAGCCTAAA AAGGTGGCAT    2700

TTGATTGCCT AGAATGGATC AGAAAGCACC ACCCATATGA TTCAGGGATA ATTTACTGCC    2760

TCTCCAGGCG AGAATGTGAC ACCATGGCTG ACACGTTACA GAGAGATGGG CTCGCTGCTC    2820

TTGCTTACCA TGCTGGCCTC AGTGATTCTG CCAGAGATGA AGTGCAGCAG AAGTGGATTA    2880

ATCAGGATGG CTGTCAGGTT ATCTGTGCTA CAATTGCATT TGGAATGGGG ATTGACAAAC    2940

CGGACGTGCG ATTTGTGATT CATGCATCTC TCCCTAAATC TGTGGAGGGT TACTACCAAG    3000

AATCTGGCAG AGCTGGAAGA GATGGGGAAA TATCTCACTG CCTGCTTTTC TATACCTATC    3060

ATGATGTGAC CAGACTGAAA AGACTTATAA TGATGGAAAA AGATGGAAAC CATCATACAA    3120

GAGAAACTCA CTTCAATAAT TTGTATAGCA TGGTACATTA CTGTGAAAAT ATAACGGAAT    3180

GCAGGAGAAT ACAGCTTTTG GCCTACTTTG GTGAAAATGG ATTTAATCCT GATTTTGTA     3240

AGAAACACCC AGATGTTTCT TGTGATAATT GCTGTAAAAC AAAGGATTAT AAAACAAGAG    3300

ATGTGACTGA CGATGTGAAA AGTATTGTAA GATTTGTTCA AGAACATAGT TCATCACAAG    3360

GAATGAGAAA TATAAAACAT GTAGGTCCTT CTGGAAGATT TACTATGAAT ATGCTGGTCG    3420

ACATTTTCTT GGGGAGTAAG AGTGCAAAAA TCCAGTCAGG TATATTTGGA AAAGGATCTG    3480

CTTATTCACG ACACAATGCC GAAAGACTTT TTAAAAAGCT GATACTTGAC AAGATTTTGG    3540

ATGAAGACTT ATATATCAAT GCCAATGACC AGGCGATCGC TTATGTGATG CTCGGAAATA    3600

AAGCCCAAAC TGTACTAAAT GGCAATTTAA AGGTAGACTT TATGGAAACA GAAAATTCCA    3660

GCAGTGTGAA AAAACAAAAA GCGTTAGTAG CAAAAGTGTC TCAGAGGGAA GAGATGGTTA    3720

AAAAATGTCT TGGAGAACTT ACAGAAGTCT GCAAATCTCT GGGGAAAGTT TTTGGTGTCC    3780

ATTACTTCAA TATTTTTAAT ACCGTCACTC TCAAGAAGCT TGCAGAATCT TTATCTTCTG    3840

ATCCTGAGGT TTTGCTTCAA ATTGATGTGT TTACTGAAGA CAAACTGGAA AAATATGGTG    3900

CGGAAGTGAT TCAGTATTA CAGAAATACT CTGAATGGAC ATCGCCAGCT GAAGACAGTT     3960
```

-continued

```
CCCCAGGGAT AAGCCTGTCC AGCAGCAGAG GCCCCGGAAG AAGTGCCGCT GAGGAGCTTG      4020

ACGAGGAAAT ACCCGTATCT TCCCACTACT TTGCAAGTAA AACCAGAAAT GAAAGGAAGA      4080

GGAAAAAGAT GCCAGCCTCC CAAAGGTCTA AGAGGAGAAA AACTGCTTCC AGTGGTTCCA      4140

AGGCAAAGGG GGGGTCTGCC ACATGTAGAA AGATATCTTC CAAAACGAAA TCCTCCAGCA      4200

TCATTGGATC CAGTTCAGCC TCACATACTT CTCAAGCGAC ATCAGGAGCC AATAGCAAAT      4260

TGGGGATTAT GGCTCCACCG AAGCCTATAA ATAGACCGTT TCTTAAGCCT TCATATGCAT      4320

TCTCATAACA ACCGAATCTC AATGTACATA GACCCTCTTT CTTGTTTGTC AGCATCTGAC      4380

CATCTGTGAC TATAAAGCTG TTATTCTTGT TATACCAAAA AAAAAAAAAA AAAAAA         4437
```

(2) INFORMATION FOR SEQ ID NO:73:

(i) SEQUENCE CHARACTERISTICS:
        (A) LENGTH: 65
        (B) TYPE: NUCLEIC ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 73:

```
GCTTCCGGCG GAAGTGAGCC AGGGCTTGGC GCGGCGGCCG TGGTTGCGGC                  50

GCGGGAAGTT TGGAT                                                       65
```

(2) INFORMATION FOR SEQ ID NO:74:

(i) SEQUENCE CHARACTERISTICS:
        (A) LENGTH: 393
        (B) TYPE: AMINO ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 74:

```
Phe Pro His Thr Lys Glu Met Met Lys Ile Phe His Lys Lys Phe
1               5                   10                  15

Gly Leu His Asn Phe Arg Thr Asn Gln Leu Glu Ala Ile Asn Ala
                20                  25                  30

Ala Leu Leu Gly Glu Asp Cys Phe Ile Leu Met Pro Thr Gly Gly
                35                  40                  45

Gly Lys Ser Leu Cys Tyr Gln Leu Pro Ala Cys Val Ser Pro Gly
                50                  55                  60
```

-continued

```
Val Thr Val Val Ile Ser Pro Leu Arg Ser Leu Ile Val Asp Gln
                65                  70                  75
Val Gln Lys Leu Thr Ser Leu Asp Ile Pro Ala Thr Tyr Leu Thr
                80                  85                  90
Gly Asp Lys Thr Asp Ser Glu Ala Thr Asn Ile Tyr Leu Gln Leu
                95                 100                 105
Ser Lys Lys Asp Pro Ile Ile Lys Leu Leu Tyr Val Thr Pro Glu
               110                 115                 120
Lys Ile Cys Ala Ser Asn Arg Leu Ile Ser Thr Leu Glu Asn Leu
               125                 130                 135
Tyr Glu Arg Lys Leu Leu Ala Arg Phe Val Ile Asp Glu Ala His
               140                 145                 150
Cys Val Ser Gln Trp Gly His Asp Phe Arg Gln Asp Tyr Lys Arg
               155                 160                 165
Met Asn Met Leu Arg Gln Lys Phe Pro Ser Val Pro Val Met Ala
               170                 175                 180
Leu Thr Ala Thr Ala Asn Pro Arg Val Gln Lys Asp Ile Leu Thr
               185                 190                 195
Gln Leu Lys Ile Leu Arg Pro Gln Val Phe Ser Met Ser Phe Asn
               200                 205                 210
Arg His Asn Leu Lys Tyr Tyr Val Leu Pro Lys Lys Pro Lys Lys
               215                 220                 225
Val Ala Phe Asp Cys Leu Glu Trp Ile Arg Lys His His Pro Tyr
               230                 235                 240
Asp Ser Gly Ile Ile Tyr Cys Leu Ser Arg Arg Glu Cys Asp Thr
               245                 250                 255
Met Ala Asp Thr Leu Gln Arg Asp Gly Leu Ala Ala Leu Ala Tyr
               260                 265                 270
His Ala Gly Leu Ser Asp Ser Ala Arg Asp Glu Val Gln Gln Lys
               275                 280                 285
Trp Ile Asn Gln Asp Gly Cys Gln Val Ile Cys Ala Thr Ile Ala
               290                 295                 300
Phe Gly Met Gly Ile Asp Lys Pro Asp Val Arg Phe Val Ile His
               305                 310                 315
Ala Ser Leu Pro Lys Ser Val Glu Gly Tyr Tyr Gln Glu Ser Gly
               320                 325                 330
Arg Ala Gly Arg Asp Gly Glu Ile Ser His Cys Leu Leu Phe Tyr
               335                 340                 345
Thr Tyr His Asp Val Thr Arg Leu Lys Arg Leu Ile Met Met Glu
               350                 355                 360
Lys Asp Gly Asn His His Thr Arg Glu Thr His Phe Asn Asn Leu
               365                 370                 375
Tyr Ser Met Val His Tyr Cys Glu Asn Ile Thr Glu Cys Arg Arg
               380                 385                 390
Ile Gln Leu
```

(2) INFORMATION FOR SEQ ID NO:75:

(i) SEQUENCE CHARACTERISTICS:
        (A) LENGTH: 386
        (B) TYPE: AMINO ACID
        (C) STRANDEDNESS: SINGLE
        (D) TOPOLOGY: LINEAR (ii) MOLECULE TYPE:

-continued (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 75:

```
Phe Pro Trp Ser Gly Lys Val Lys Asp Ile Leu Gln Asn Val Phe
  1               5                  10                  15

Lys Leu Glu Lys Phe Arg Pro Leu Gln Leu Glu Thr Ile Asn Val
                 20                  25                  30

Thr Met Ala Gly Lys Glu Val Phe Leu Val Met Pro Thr Gly Gly
                 35                  40                  45

Gly Lys Ser Leu Cys Tyr Gln Leu Pro Ala Leu Cys Ser Asp Gly
                 50                  55                  60

Phe Thr Leu Val Ile Cys Pro Leu Ile Ser Leu Met Glu Asp Gln
                 65                  70                  75

Leu Met Val Leu Lys Gln Leu Gly Ile Ser Ala Thr Met Leu Asn
                 80                  85                  90

Ala Ser Ser Ser Lys Glu His Val Lys Trp Val His Asp Glu Met
                 95                 100                 105

Val Asn Lys Asn Ser Glu Leu Lys Leu Ile Tyr Val Thr Pro Glu
                110                 115                 120

Lys Ile Ala Lys Ser Lys Met Phe Met Ser Arg Leu Glu Lys Ala
                125                 130                 135

Tyr Glu Ala Arg Arg Phe Thr Arg Ile Ala Val Asp Glu Val His
                140                 145                 150

Cys Cys Ser Gln Trp Gly His Asp Phe Arg Pro Asp Tyr Lys Ala
                155                 160                 165

Leu Gly Ile Leu Lys Arg Gln Phe Pro Asn Ala Ser Leu Ile Gly
                170                 175                 180

Leu Thr Ala Thr Ala Thr Asn His Val Leu Thr Asp Ala Gln Lys
                185                 190                 195

Ile Leu Cys Ile Glu Lys Cys Phe Thr Phe Thr Ala Ser Phe Asn
                200                 205                 210

Arg Pro Asn Leu Tyr Tyr Glu Val Arg Gln Lys Pro Ser Asn Thr
                215                 220                 225

Glu Asp Phe Ile Glu Asp Ile Val Lys Leu Ile Asn Gly Arg Tyr
                230                 235                 240

Lys Gly Gln Ser Gly Ile Ile Tyr Cys Phe Ser Gln Lys Asp Ser
                245                 250                 255

Glu Gln Val Thr Val Ser Leu Gln Asn Leu Gly Ile His Ala Gly
                260                 265                 270

Ala Tyr His Ala Asn Leu Glu Pro Glu Asp Lys Thr Thr Val His
                275                 280                 285

Arg Lys Trp Ser Ala Asn Glu Ile Gln Val Val Val Ala Thr Val
                290                 295                 300

Ala Phe Gly Met Gly Ile Asp Lys Pro Asp Val Arg Phe Val Ile
                305                 310                 315

His His Ser Met Ser Lys Ser Met Glu Asn Tyr Tyr Gln Glu Ser
                320                 325                 330
```

```
Gly Arg Ala Gly Arg Asp Asp Met Lys Ala Asp Cys Ile Leu Tyr
                335                 340                 345

Tyr Gly Phe Gly Asp Ile Phe Arg Ile Ser Ser Met Val Val Met
                350                 355                 360

Glu Asn Val Gly Gln Gln Lys Leu Tyr Glu Met Val Ser Tyr Cys
                365                 370                 375

Gln Asn Ile Ser Lys Ser Arg Arg Val Leu Met
                380                 385
```

(2) INFORMATION FOR SEQ ID NO:76:

(i) SEQUENCE CHARACTERISTICS:
        (A) LENGTH: 393
        (B) TYPE: AMINO ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 76:

```
Tyr Pro Trp Ser Asp Glu Val Leu Tyr Arg Leu His Glu Val Phe
1               5                   10                  15

Lys Leu Pro Gly Phe Arg Pro Asn Gln Leu Glu Ala Val Asn Ala
                20                  25                  30

Thr Leu Gln Gly Lys Asp Val Phe Val Leu Met Pro Thr Gly Gly
                35                  40                  45

Gly Lys Ser Leu Cys Tyr Gln Leu Pro Ala Val Val Lys Ser Gly
                50                  55                  60

Lys Thr His Gly Thr Thr Ile Val Ile Ser Pro Leu Ile Ser Leu
                65                  70                  75

Met Gln Asp Gln Val Glu His Leu Leu Asn Lys Asn Ile Lys Ala
                80                  85                  90

Ser Met Phe Ser Ser Arg Gly Thr Ala Glu Gln Arg Arg Gln Thr
                95                  100                 105

Phe Asn Leu Phe Ile Asn Gly Leu Leu Asp Leu Val Tyr Ile Ser
                110                 115                 120

Pro Glu Met Ile Ser Ala Ser Glu Gln Cys Lys Arg Ala Ile Ser
                125                 130                 135

Arg Leu Tyr Ala Asp Gly Lys Leu Ala Arg Ile Val Val Asp Glu
                140                 145                 150

Ala His Cys Val Ser Asn Trp Gly His Asp Phe Arg Pro Asp Tyr
                155                 160                 165

Lys Glu Leu Lys Phe Phe Lys Arg Glu Tyr Pro Asp Ile Pro Met
                170                 175                 180

Ile Ala Leu Thr Ala Thr Ala Ser Glu Gln Val Arg Met Asp Ile
                185                 190                 195

Ile His Asn Leu Glu Leu Lys Glu Pro Val Phe Leu Lys Gln Ser
                200                 205                 210
```

-continued

```
Phe Asn Arg Thr Asn Leu Tyr Tyr Glu Val Asn Lys Lys Thr Lys
                215                 220                 225

Asn Thr Ile Phe Glu Ile Cys Asp Ala Val Lys Ser Arg Phe Lys
                230                 235                 240

Asn Gln Thr Gly Ile Ile Tyr Cys His Ser Lys Lys Ser Cys Glu
                245                 250                 255

Gln Thr Ser Ala Gln Met Gln Arg Asn Gly Ile Lys Cys Ala Tyr
                260                 265                 270

Tyr His Ala Gly Met Glu Pro Asp Glu Arg Leu Ser Val Gln Lys
                275                 280                 285

Ala Trp Gln Ala Asp Glu Ile Gln Val Ile Cys Ala Thr Val Ala
                290                 295                 300

Phe Gly Met Gly Ile Asp Lys Pro Asp Val Arg Phe Val Tyr His
                305                 310                 315

Phe Thr Val Pro Arg Thr Leu Glu Gly Tyr Tyr Gln Glu Thr Gly
                320                 325                 330

Arg Ala Gly Arg Asp Gly Asp Tyr Ser Tyr Cys Ile Thr Tyr Phe
                335                 340                 345

Ser Phe Arg Asp Ile Arg Thr Met Gln Thr Met Ile Gln Lys Asp
                350                 355                 360

Lys Asn Leu Asp Arg Glu Asn Lys Glu Lys His Leu Asn Lys Leu
                365                 370                 375

Gln Gln Val Met Ala Tyr Cys Asp Asn Val Thr Asp Cys Arg Arg
                380                 385                 390

Lys Leu Val
```

(2) INFORMATION FOR SEQ ID NO:77:

(i) SEQUENCE CHARACTERISTICS:
  (A) LENGTH: 370
  (B) TYPE: AMINO ACID
  (C) STRANDEDNESS: SINGLE
  (D) TOPOLOGY: LINEAR (ii) MOLECULE TYPE:
  (A) DESCRIPTION: OTHER NUCLEIC ACID (iii) HYPOTHETICAL: YES (iv) ANTI-SENSE: NO (ix) FEATURE:
  (A) NAME/KEY:
  (B) LOCATION:
  (C) IDENTIFICATION METHOD:
  (D) OTHER INFORMATION:

(xi) SEQUENCE DESCRIPTION: SEQ ID NO: 77:

```
Val Leu Gln Glu Thr Phe Gly Tyr Gln Gln Phe Arg Pro Gly Gln
1               5                   10                  15

Glu Glu Ile Ile Asp Thr Val Leu Ser Gly Arg Asp Cys Leu Val
                20                  25                  30

Val Met Pro Thr Gly Gly Gly Lys Ser Leu Cys Tyr Gln Ile Pro
                35                  40                  45

Ala Leu Leu Leu Asn Gly Leu Thr Val Val Val Ser Pro Leu Ile
                50                  55                  60

Ser Leu Met Lys Asp Gln Val Asp Gln Leu Gln Ala Asn Gly Val
                65                  70                  75

Ala Ala Ala Cys Leu Asn Ser Thr Gln Thr Arg Glu Gln Gln Leu
                80                  85                  90
```

```
Glu Val Met Thr Gly Cys Arg Thr Gly Gln Ile Arg Leu Leu Tyr
                 95                 100                105

Ile Ala Pro Glu Arg Leu Met Leu Asp Asn Phe Leu Glu His Leu
            110                 115                120

Ala His Trp Asn Pro Val Leu Leu Ala Val Asp Glu Ala His Cys
            125                 130                135

Ile Ser Gln Trp Gly His Asp Phe Arg Pro Glu Tyr Ala Ala Leu
            140                 145                150

Gly Gln Leu Arg Gln Arg Phe Pro Thr Leu Pro Phe Met Ala Leu
            155                 160                165

Thr Ala Thr Ala Asp Asp Thr Thr Arg Gln Asp Ile Val Arg Leu
            170                 175                180

Leu Gly Leu Asn Asp Pro Leu Ile Gln Ile Ser Ser Phe Asp Arg
            185                 190                195

Pro Asn Ile Arg Tyr Met Leu Met Glu Lys Phe Lys Pro Leu Asp
            200                 205                210

Gln Leu Met Arg Tyr Val Gln Glu Gln Arg Gly Lys Ser Gly Ile
            215                 220                225

Ile Tyr Cys Asn Ser Arg Ala Lys Val Glu Asp Thr Ala Ala Ala
            230                 235                240

Leu Gln Ser Lys Gly Ile Ser Ala Ala Ala Tyr His Ala Gly Leu
            245                 250                255

Glu Asn Asn Val Arg Ala Asp Val Gln Glu Lys Phe Gln Arg Asp
            260                 265                270

Asp Leu Gln Ile Val Val Ala Thr Val Ala Phe Gly Met Gly Ile
            275                 280                285

Asn Lys Pro Asn Val Arg Phe Val Val His Phe Asp Ile Pro Arg
            290                 295                300

Asn Ile Glu Ser Tyr Tyr Gln Glu Thr Gly Arg Ala Gly Arg Asp
            305                 310                315

Gly Leu Pro Ala Glu Ala Met Leu Phe Tyr Asp Pro Ala Asp Met
            320                 325                330

Ala Trp Leu Arg Arg Cys Leu Glu Glu Lys Pro Gln Gly Gln Leu
            335                 340                345

Gln Asp Ile Glu Arg His Lys Leu Asn Ala Met Gly Ala Phe Ala
            350                 355                360

Glu Ala Gln Thr Cys Arg Arg Leu Val Leu
            365                 370
```

(2) INFORMATION FOR SEQ ID NO:78:

(i) SEQUENCE CHARACTERISTICS:
        (A) LENGTH: 1417
        (B) TYPE: AMINO ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 78:

```
            Met Ala Ala Val Pro Gln Asn Asn Leu Gln Glu Gln
            1               5                   10
Leu Glu Arg His Ser Ala Arg Thr Leu Asn Asn Lys Leu Ser Leu Ser
            15                  20                  25
Lys Pro Lys Phe Ser Gly Phe Thr Phe Lys Lys Thr Ser Ser Asp
30                      35                  40
Asn Asn Val Ser Val Thr Asn Val Ser Val Ala Lys Thr Pro Val Leu
45                      50                  55                  60
Arg Asn Lys Asp Val Asn Val Thr Glu Asp Phe Ser Phe Ser Glu Pro
                65                  70                  75
Leu Pro Asn Thr Thr Asn Gln Gln Arg Val Lys Asp Phe Lys Asn
            80                  85                  90
Ala Pro Ala Gly Gln Glu Thr Gln Arg Gly Gly Ser Lys Ser Leu Leu
            95                      100                 105
Pro Asp Phe Leu Gln Thr Pro Lys Glu Val Val Cys Thr Thr Gln Asn
    110                 115                 120
Thr Pro Thr Val Lys Lys Ser Arg Asp Thr Ala Leu Lys Lys Leu Glu
125                 130                 135                 140
Phe Ser Ser Ser Pro Asp Ser Leu Ser Thr Ile Asn Asp Trp Asp Asp
                145                 150                 155
Met Asp Asp Phe Asp Thr Ser Glu Thr Ser Lys Ser Phe Val Thr Pro
                160                 165                 170
Pro Gln Ser His Phe Val Arg Val Ser Thr Ala Gln Lys Ser Lys Lys
            175                 180                 185
Gly Lys Arg Asn Phe Phe Lys Ala Gln Leu Tyr Thr Thr Asn Thr Val
    190                 195                 200
Lys Thr Asp Leu Pro Pro Pro Ser Ser Glu Ser Glu Gln Ile Asp Leu
205                 210                 215                 220
Thr Glu Glu Gln Lys Asp Asp Ser Glu Trp Leu Ser Ser Asp Val Ile
                225                 230                 235
Cys Ile Asp Asp Gly Pro Ile Ala Glu Val His Ile Asn Glu Asp Ala
                240                 245                 250
Gln Glu Ser Asp Ser Leu Lys Thr His Leu Glu Asp Glu Arg Asp Asn
            255                 260                 265
Ser Glu Lys Lys Lys Asn Leu Glu Glu Ala Glu Leu His Ser Thr Glu
    270                 275                 280
Lys Val Pro Cys Ile Glu Phe Asp Asp Asp Tyr Asp Thr Asp Phe
285                 290                 295                 300
Val Pro Pro Ser Pro Glu Ile Ile Ser Ala Ser Ser Ser Ser
                305                 310                 315
Lys Cys Leu Ser Thr Leu Lys Asp Leu Asp Thr Ser Asp Arg Lys Glu
            320                 325                 330
Asp Val Leu Ser Thr Ser Lys Asp Leu Leu Ser Lys Pro Glu Lys Met
            335                 340                 345
Ser Met Gln Glu Leu Asn Pro Glu Thr Ser Thr Asp Cys Asp Ala Arg
    350                 355                 360
Gln Ile Ser Leu Gln Gln Leu Ile His Val Met Glu His Ile Cys
365                 370                 375                 380
Lys Leu Ile Asp Thr Ile Pro Asp Asp Lys Leu Lys Leu Leu Asp Cys
                385                 390                 395
Gly Asn Glu Leu Leu Gln Gln Arg Asn Ile Arg Arg Lys Leu Leu Thr
```

```
                    400              405              410
Glu Val Asp Phe Asn Lys Ser Asp Ala Ser Leu Leu Gly Ser Leu Trp
            415              420              425

Arg Tyr Arg Pro Asp Ser Leu Asp Gly Pro Met Glu Gly Asp Ser Cys
        430              435              440

Pro Thr Gly Asn Ser Met Lys Glu Leu Asn Phe Ser His Leu Pro Ser
445              450              455              460

Asn Ser Val Ser Pro Gly Asp Cys Leu Leu Thr Thr Leu Gly Lys
                465              470              475

Thr Gly Phe Ser Ala Thr Arg Lys Asn Leu Phe Glu Arg Pro Leu Phe
            480              485              490

Asn Thr His Leu Gln Lys Ser Phe Val Ser Ser Asn Trp Ala Glu Thr
        495              500              505

Pro Arg Leu Gly Lys Lys Asn Glu Ser Ser Tyr Phe Pro Gly Asn Val
510              515              520

Leu Thr Ser Thr Ala Val Lys Asp Gln Asn Lys His Thr Ala Ser Ile
525              530              535              540

Asn Asp Leu Glu Arg Glu Thr Gln Pro Ser Tyr Asp Ile Asp Asn Phe
                545              550              555

Asp Ile Asp Asp Phe Asp Asp Asp Asp Trp Glu Asp Ile Met His
            560              565              570

Asn Leu Ala Ala Ser Lys Ser Ser Thr Ala Ala Tyr Gln Pro Ile Lys
        575              580              585

Glu Gly Arg Pro Ile Lys Ser Val Ser Glu Arg Leu Ser Ser Ala Lys
        590              595              600

Thr Asp Cys Leu Pro Val Ser Ser Thr Ala Gln Asn Ile Asn Phe Ser
605              610              615              620

Glu Ser Ile Gln Asn Tyr Thr Asp Lys Ser Ala Gln Asn Leu Ala Ser
            625              630              635

Arg Asn Leu Lys His Glu Arg Phe Gln Ser Leu Ser Phe Pro His Thr
                640              645              650

Lys Glu Met Met Lys Ile Phe His Lys Lys Phe Gly Leu His Asn Phe
            655              660              665

Arg Thr Asn Gln Leu Glu Ala Ile Asn Ala Ala Leu Leu Gly Glu Asp
        670              675              680

Cys Phe Ile Leu Met Pro Thr Gly Gly Gly Lys Ser Leu Cys Tyr Gln
685              690              695              700

Leu Pro Ala Cys Val Ser Pro Gly Val Thr Val Val Ile Ser Pro Leu
                705              710              715

Arg Ser Leu Ile Val Asp Gln Val Gln Lys Leu Thr Ser Leu Asp Ile
            720              725              730

Pro Ala Thr Tyr Leu Thr Gly Asp Lys Thr Asp Ser Glu Ala Thr Asn
        735              740              745

Ile Tyr Leu Gln Leu Ser Lys Lys Asp Pro Ile Ile Lys Leu Leu Tyr
        750              755              760

Val Thr Pro Glu Lys Ile Cys Ala Ser Asn Arg Leu Ile Ser Thr Leu
765              770              775              780

Glu Asn Leu Tyr Glu Arg Lys Leu Leu Ala Arg Phe Val Ile Asp Glu
                785              790              795

Ala His Cys Val Ser Gln Trp Gly His Asp Phe Arg Gln Asp Tyr Lys
            800              805              810

Arg Met Asn Met Leu Arg Gln Lys Phe Pro Ser Val Pro Val Met Ala
        815              820              825
```

```
Leu Thr Ala Thr Ala Asn Pro Arg Val Gln Lys Asp Ile Leu Thr Gln
830                 835                 840

Leu Lys Ile Leu Arg Pro Gln Val Phe Ser Met Ser Phe Asn Arg His
845                 850                 855                 860

Asn Leu Lys Tyr Tyr Val Leu Pro Lys Lys Pro Lys Lys Val Ala Phe
                865                 870                 875

Asp Cys Leu Glu Trp Ile Arg Lys His His Pro Tyr Asp Ser Gly Ile
                880                 885                 890

Ile Tyr Cys Leu Ser Arg Arg Glu Cys Asp Thr Met Ala Asp Thr Leu
                895                 900                 905

Gln Arg Asp Gly Leu Ala Ala Leu Ala Tyr His Ala Gly Leu Ser Asp
910                 915                 920

Ser Ala Arg Asp Glu Val Gln Gln Lys Trp Ile Asn Gln Asp Gly Cys
925                 930                 935                 940

Gln Val Ile Cys Ala Thr Ile Ala Phe Gly Met Gly Ile Asp Lys Pro
                945                 950                 955

Asp Val Arg Phe Val Ile His Ala Ser Leu Pro Lys Ser Val Glu Gly
                960                 965                 970

Tyr Tyr Gln Glu Ser Gly Arg Ala Gly Arg Asp Gly Glu Ile Ser His
                975                 980                 985

Cys Leu Leu Phe Tyr Thr Tyr His Asp Val Thr Arg Leu Lys Arg Leu
990                 995                 1000

Ile Met Met Glu Lys Asp Gly Asn His His Thr Arg Glu Thr His Phe
1005                1010                1015                1020

Asn Asn Leu Tyr Ser Met Val His Tyr Cys Glu Asn Ile Thr Glu Cys
                1025                1030                1035

Arg Arg Ile Gln Leu Leu Ala Tyr Phe Gly Glu Asn Gly Phe Asn Pro
                1040                1045                1050

Asp Phe Cys Lys Lys His Pro Asp Val Ser Cys Asp Asn Cys Cys Lys
                1055                1060                1065

Thr Lys Asp Tyr Lys Thr Arg Asp Val Thr Asp Asp Val Lys Ser Ile
                1070                1075                1080

Val Arg Phe Val Gln Glu His Ser Ser Ser Gln Gly Met Arg Asn Ile
1085                1090                1095                1100

Lys His Val Gly Pro Ser Gly Arg Phe Thr Met Asn Met Leu Val Asp
                1105                1110                1115

Ile Phe Leu Gly Ser Lys Ser Ala Lys Ile Gln Ser Gly Ile Phe Gly
                1120                1125                1130

Lys Gly Ser Ala Tyr Ser Arg His Asn Ala Glu Arg Leu Phe Lys Lys
                1135                1140                1145

Leu Ile Leu Asp Lys Ile Leu Asp Glu Asp Leu Tyr Ile Asn Ala Asn
                1150                1155                1160

Asp Gln Ala Ile Ala Tyr Val Met Leu Gly Asn Lys Ala Gln Thr Val
1165                1170                1175                1180

Leu Asn Gly Asn Leu Lys Val Asp Phe Met Glu Thr Glu Asn Ser Ser
                1185                1190                1195

Ser Val Lys Lys Gln Lys Ala Leu Val Ala Lys Val Ser Gln Arg Glu
                1200                1205                1210

Glu Met Val Lys Lys Cys Leu Gly Glu Leu Thr Glu Val Cys Lys Ser
                1215                1220                1225

Leu Gly Lys Val Phe Gly Val His Tyr Phe Asn Ile Phe Asn Thr Val
                1230                1235                1240
```

```
Thr Leu Lys Lys Leu Ala Glu Ser Leu Ser Ser Asp Phe Glu Val Leu
1245                1250                1255                1260

Leu Gln Ile Asp Gly Val Thr Glu Asp Lys Leu Glu Lys Tyr Gly Ala
                1265                1270                1275

Glu Val Ile Ser Val Leu Gln Lys Tyr Ser Glu Trp Thr Ser Pro Ala
                1280                1285                1290

Glu Asp Ser Ser Pro Gly Ile Ser Leu Ser Ser Ser Arg Gly Pro Gly
            1295                1300                1305

Arg Ser Ala Ala Glu Glu Leu Asp Glu Glu Ile Pro Val Ser Ser His
        1310                1315                1320

Tyr Phe Ala Ser Lys Thr Arg Asn Glu Arg Lys Arg Lys Lys Met Pro
1325                1330                1335                1340

Ala Ser Gln Arg Ser Lys Arg Arg Lys Thr Ala Ser Ser Gly Ser Lys
                1345                1350                1355

Ala Lys Gly Gly Ser Ala Thr Cys Arg Lys Ile Ser Ser Lys Thr Lys
                1360                1365                1370

Ser Ser Ser Ile Ile Gly Ser Ser Ser Ala Ser His Thr Ser Gln Ala
            1375                1380                1385

Thr Ser Gly Ala Asn Ser Lys Leu Gly Ile Met Ala Pro Pro Lys Pro
    1390                1395                1400

Ile Asn Arg Pro Phe Leu Lys Pro Ser Tyr Ala Phe Ser
1405                1410                1415
```